United States Patent [19]

Lewis et al.

[11] Patent Number: 5,308,864
[45] Date of Patent: May 3, 1994

[54] 6-(HYDRONAPHTYL-1-ETHYL)-4-HYDROXY-3,4,5,6-TETRAHYDRO-2H-PYRAN-2-ONES AND THE CORRESPONDING HYDROXY ACIDS

[75] Inventors: Christopher N. Lewis; Alan H. Davidson, both of Oxford; Christopher D. Floyd; Jonathan P. Dickens, both of Buckinghamshire, all of England

[73] Assignee: British Bio-Technology Limited, Oxford, England

[21] Appl. No.: 773,657
[22] PCT Filed: Jul. 4, 1990
[86] PCT No.: PCT/GB90/01030
  § 371 Date: Oct. 15, 1991
  § 102(e) Date: Oct. 15, 1991
[87] PCT Pub. No.: WO91/00280
  PCT Pub. Date: Jan. 10, 1991

[30] Foreign Application Priority Data

Jul. 4, 1989 [GB] United Kingdom ............... 8915280

[51] Int. Cl.⁵ .................. A61K 31/35; A61K 31/215; A61K 31/225; C07D 309/30
[52] U.S. Cl. ..................... 514/460; 514/529; 549/292; 560/84; 560/181
[58] Field of Search ............... 549/292, 214; 560/84, 560/181; 514/460, 529

[56] References Cited

U.S. PATENT DOCUMENTS

| 4,293,496 | 10/1981 | Willard | 549/292 |
|---|---|---|---|
| 4,444,784 | 4/1984 | Hoffman et al. | 549/292 |
| 4,661,483 | 4/1987 | Hoffman et al. | 549/292 |
| 4,668,699 | 5/1987 | Hoffman et al. | 514/460 |
| 4,771,071 | 9/1988 | Hoffman et al. | 514/460 |

FOREIGN PATENT DOCUMENTS 0142146 11/1984 European Pat. Off.
0251625 6/1987 European Pat. Off.

OTHER PUBLICATIONS

A. Endo et al., J. Antibiotics, 29:1346–1348, Dec. 1976.
A. W. Alberts et al., J. Proc. Nat'l. Acad. Sci. USA, 77:3957, Jul. 1980.
Y. K. Tong Lam et al., J. Antibiotics, 34:614–616, May 1981.
G. Albers-Schonberg et al., J. Antibiotics, 34:507–512, May 1981.
N. Serizawa et al., J. Antibiotics, 36:604–607, May 1983.
W. F. Hoffman et al., J. Med. Chem., 29:849–852 (1986).
K. Chen et al., Chemistry Letters, 1923–1926 (1987).
Davidson et al., J. Chem. Soc. Chem. Commun., 1987, 1786.
Kleinsek et al., Proc. Nat'l. Acad. Sci. USA, 74(4):1431–1435, Apr. 1977.
T. Rosen and C. H. Heathcock, Tetrahedron, 42:4909–4951 (1986).
P. D. Theisen and C. H. Heathcock, J. Org. Chem., 53:2374–2378 (1988).

*Primary Examiner*—C. Warren Ivy
*Assistant Examiner*—A. A. Owens
*Attorney, Agent, or Firm*—Allegretti & Witcoff, Ltd.

[57] ABSTRACT

Compounds of either of general formulae (I) and (II), wherein: $R^1$ represents a $C_{1-8}$ alkyl, $C_{3-8}$ cycloalkyl, $C_{3-8}$ cycloalkyl($C_{1-8}$)alkyl, $C_{2-8}$ alkenyl, or $C_{1-6}$ alkyl substituted phenyl group; $R^2$ represents a $C_{1-8}$ alkyl, $C_{2-8}$ alkenyl, $C_{2-8}$alkynyl group or a $C_{1-5}$ alkyl, $C_{2-5}$ alkenyl or $C_{2-5}$ alkynyl group substituted with a substituted phenyl group; $R^3$ represents a hydrogen atom or a substituent $R^4$ or M; $R^4$ represents a $C_{1-5}$ alkyl group, or $C_{1-5}$ alkyl group substituted with a group chosen from substituted phenyl, dimethylamino and acetylamino; $R^5$ represents a hydrogen atom or a methyl or ethyl group except that when $R^2$ is methyl then $R^5$ is not methyl; M represents a cation capable of forming a pharmaceutically acceptable salt; Q represents C=O or CHOH; and each of a, b, c, and d, is independently a single or double bond except that when a and c are double bonds then b is a single bond; are inhibitors of the enzyme 3-hydroxy-3-methylglutaryl coenzyme A reductase (HMG-CoA reductase), the rate limiting enzyme in the biosynthesis of cholesterol in mammals including man, and as such are useful in the treatment of hypercholesterolemia in general and arteriosclerosis, familiar hypercholesterolemia or hyperlipidemia in particular.

14 Claims, 7 Drawing Sheets

SCHEME VI

SCHEME VII

6-(HYDRONAPHTYL-1-ETHYL)-4-HYDROXY-3,4,5,6-TETRAHYDRO-2H-PYRAN-2-ONES AND THE CORRESPONDING HYDROXY ACIDS

This invention relates to pharmaceutically active compounds, which are substituted decalins. The compounds of the present invention are inhibitors of the enzyme 3-hydroxy-3-methylglutaryl coenzyme A reductase (HMG-CoA reductase), the rate limiting enzyme in the biosynthesis of cholesterol in mammals including man, and as such are useful in the treatment of hypercholesterolaemia and hyperlipidaemia. Clinical evidence shows that reduction of serum cholesterol levels lead to a decreased risk of heat disease.

The natural fermentation products compactin (disclosed by A. Endo, et al. in *Journal of Antibiotics*, 29, 1346-1348 (1976) and mevinolin (disclosed by A. W. Alberts, et al. in *J. Proc. Natl. Acad. Sci. U.S.A.*, 77, 3957 (1980)) are very active antihypercholesterolaemic agents which limit cholesterol biosynthesis by inhibiting the enzyme 3-hydroxy-3-methylglutaryl coenzyme A (HMG-CoA) reductase, the rate-limiting enzyme and natural point of cholesterolgenesis regulation in mammals, including man. Compactin (R=H, a=double bond) and mevinolin (R=α-CH₃, a=double bond; also known as lovastatin) have the structures shown below:

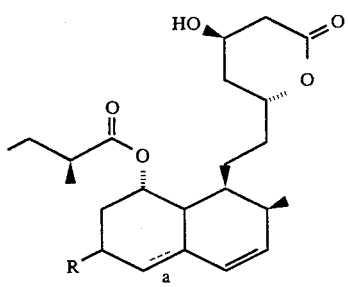

Also known in the art are the natural products dihydrocompactin (R=H, a=single bond) disclosed by Y. K. T. Lam et al., *Journal of Antibiotics*, 34, 614-616 (1981), dihydromevinolin (R=α-CH₃, a=single bond) disclosed by G. Albers-Schonberg et al., *Journal of Antibiotics*, 34, 507-512 (1981), and eptastatin (R=β-OH, a=double bond) disclosed by N. Serizawa et al., in *Journal of Antibiotics*, 36, 604-607 (1983).

U.S. Pat. No. 4,293,496 (Willard) disclosed a number of semisynthetic analogues of mevinolin having the structure

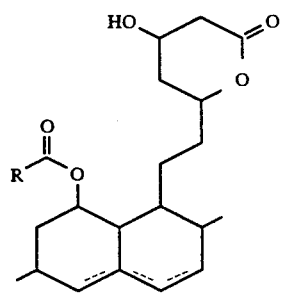

where the dotted lines represent single or double bonds and R is $C_{1-8}$ straight chain alkyl, $C_{3-10}$ branched chain alkyl except (S)-2-butyl, $C_{3-10}$ cycloalkyl, $C_{2-10}$ alkenyl, $C_{1-10}$ $CF_3$ substituted alkyl, halophenyl, phenyl $C_{1-3}$ alkyl and substituted phenyl $C_{1-3}$ alkyl.

U.S. Pat. Nos. 4,444,784, 4,661,483, 4,668,699 and 4,771,071 (Hoffman) disclose compounds of similar structure where the R group contains extra functional groups, for example ether, amide and ester groups. In *J. Med. Chem.*, 29, 849-852 (1986), W. F. Hoffman et al. report the synthesis and testing of a number of the analogues referred to above, the preferred compound (now known as simvastatin) have the structure

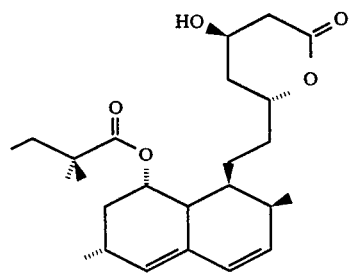

EP-A-0251625 (Inamine) discloses compounds of structure

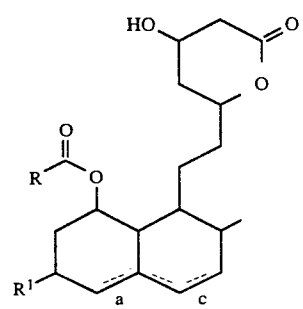

where R is similar to the corresponding group in the compounds described above, $R^1$ is a group of formula $CH_2OH$, $CH_2OCO.R^3$, $CO_2R^4$ or $CO.NR^6R^7$ wherein $R^3$, $R^4$, $R^6$, and $R^7$ can cover a range of alkyl, alkoxy, or aryl groups, and the dotted lines represent single or double bonds. Only one of these compounds, in which $R^1$ is $CH_2OCO.NHPh$, R is 1,1-dimethylpropyl and a and c are double bonds has a disclosed activity better than that of mevinolin. In general, the above patent publications also cover compounds in which the delta lactone has been hydrolysed to a delta hydroxy acid or a salt of that acid.

EP-A-0142146 disclosed compounds of structure

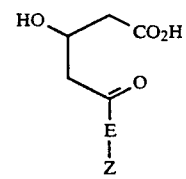

where E is $-CH_2-CH_2-$, $-CH=CH-$ or $-(CH_2)_3-$ and Z is (amongst others) a substituted decalin system of the same form as in those compounds referred to above.

None of the cited patents and articles disclose or suggest the possibility of preparing the compounds of the present invention. The unique pattern of substituents on the decalin ring system differs from the cited art, whilst the compounds exhibit potent HMG-CoA activity.

The present invention provides novel decalin based compounds which are potent inhibitors of the enzyme 3-hydroxy-3-methylglutaryl coenzyme A (HMG-CoA) reductase and, therefore, are useful in the treatment or prevention of hypercholesterolaemia, hyperlipoproteinaemia and atherosclerosis.

According to a first aspect of the invention, there is provided a compound of either of general formula I and II:

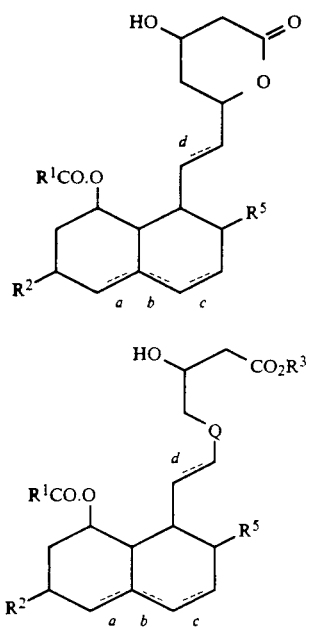

wherein:
- $R^1$ represents a $C_{1-8}$ alkyl, $C_{3-8}$ cycloalkyl, $C_{3-8}$ cycloalkyl($C_{1-8}$)alkyl, $C_{2-8}$ alkenyl, or $C_{1-6}$ alkyl substituted phenyl group;
- $R^2$ represents a $C_{1-8}$ alkyl, $C_{2-8}$ alkenyl, $C_{2-8}$ alkynyl, group or a $C_{1-5}$ alkyl, $C_{205}$ alkenyl, or $C_{2-5}$ alkynyl group substituted with a substituted phenyl grip;
- $R^3$ represents a hydrogen atom or a substituent $R^4$ or M;
- $R^4$ represents a $C_{1-5}$ alkyl group, or a $C_{1-5}$ alkyl group substituted with a group chosen from substituted phenyl, dimethylamino and acetylamino;
- $R^5$ represents a hydrogen atom or a methyl or ethyl group, except that when $R^2$ is methyl then $R^5$ is not methyl;
- M represents a cation capable of forming a p: armaceutically acceptable salt;
- Q represents C=O or CHOH; and
- each of a, b, c, and d is independently a single or double bond except that when a and c are double bonds then b is a single bond.

The term "$C_{1-8}$ alkyl" refers to a straight or branched chain alkyl moiety having one to eight carbon atoms, including for example, methyl, ethyl, propyl, isopropyl, butyl, sec-butyl, pentyl, dimethyl-propyl, hexyl, and octyl, and cognate terms (such as "$C_{1-8}$ alkoxy") are to be construed accordingly.

The term "$C_{3-8}$ cycloalkyl" refers to a saturated alicyclic moiety having from 3 to 8 carbon atoms arranged in a ring and includes, for example, cyclopropyl, cyclobutyl, cyclopentyl, and cyclooctyl.

The term "$C_{2-8}$ alkenyl" refers to a straight or branched chain alkyl moiety having one to eight carbon atoms and having in addition at least one double bond, of either E or Z stereochemistry where applicable. This term would include, for example, vinyl, 1-propenyl, 1- and 2-butenyl and 2-methyl-2-propenyl.

The term "$C_{2-8}$ alkynyl" refers to a straight or branched chain alkyl moiety having one to eight carbon atoms and having in addition at least one triple bond. This term would include, for example, propargyl, and 1- and 2-butynyl.

The term ¢substituted", as applied to a phenyl or other aromatic ring, means substituted with up to four substituents each of which independently may be $C_{1-6}$ alkyl, $C_{1-6}$ alkoxy, hydroxy, thiol, amino, halo (including fluoro, chloro, bromo, and iodo), trifluoromethyl or nitro.

The phrase "a pharmaceutically acceptable salt" as used herein and in the claims is intended to include non-toxic alkali metal salts such as sodium, potassium, calcium and magnesium, the ammonium salt and salts with non-toxic amines such as trialkylamines, dibenzylamine, pyridine, N-methylmorpholine, N-methylpiperidine and other amines which have been or can be used to form salts of carboxylic acids.

There are several chiral centres in the compounds according to the invention because of the presence of asymmetric carbon atoms. The presence of several asymmetric carbon atoms gives rise to a number of diastereoisomers with the appropriate R or S designated stereochemistry at each asymmetric centre. General Formulae I and II and, where appropriate, all other formulae in this specification are to be understood to include all such stereoisomers and mixtures (for example racemic mixtures) thereof.

Disregarding any asymmetric centres that may be present in the groups $R^1$, $R^2$, $R^3$ and $R^4$, the preferred relative and absolute stereochemistry is as shown in formula III, mutatis mutandis. More specifically for the compound III the Cahn, Ingold, Prelog designations for the absolute configurations are 4'(R), 6'(R), 1(S), 2(S), 4a(R), 6(S), 8(S), 8a(S).

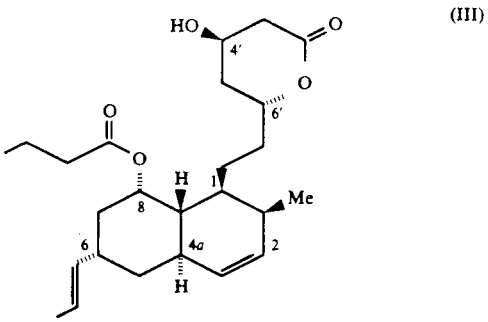

It is preferred that all of the compounds of general formulae I and II should have (wherever possible) the same spacial orientation of groups at each chiral carbon atoms and therefore belong to the same stereochemical series. The R-S designation for each center may not be identical to that found for compound III because of the details of the sequence rules for determining that designation. Clearly in compounds in which a or b are double bonds then the carbon atom labelled C-4a will not be an asymmetric centre, and in compounds of Formula II in which Q in the group C=O then the carbon atom labelled C-6' is not an asymmetric centre.

In compounds of Formula II in which Q is the group CHOH, the preferred stereochemistry is that in which the two carbon atoms bearing the hydroxy groups have the same spacial arrangement as the corresponding carbon atoms in the lactone in compound III. The preferred isomer is referred to as the syn diol.

Each M is preferably free from centres of asymmetry and is more preferably sodium, potassium or ammonium, and most preferably sodium. For simplicity, each formula in which an M appears has been written as if M were monovalent and, preferably, it is. However, M may also be divalent or trivalent and, when it is, it balances the charge of two or three carboxylic acid groups, respectively. Thus Formula II and every other formula containing an M embraces compounds wherein M is divalent or trivalent, e.g. compounds containing two or three mono carboxylate-containing anions per cation M.

Preferred compounds include those in which independently or in any combination:

$R^1$ represents $C_{4-6}$ branched alkyl;

$R^2$ represents $C_{2-6}$ alkenyl or $C_{2-5}$ alkenyl substituted with substituted phenyl;

$R^3$ is $R^4$ $R^4$ represents $C_{1-5}$ alkyl and more preferably methyl or ethyl;

Q represents CHOH; and/or b and d are both single bonds, and one or both of a and c are double bonds.

A preferred subgroup or compounds of either general formula I or of general formula II are those wherein $R^1$ represents a $C_{4-6}$ branched alkyl group; $R^2$ represents a $C_{2-6}$ alkenyl group; each of a and c independently represents a single or double bond; and each of b and d represents a single bond. Illustrative compounds of this subgroup are:

(A) (1S,2S,4aR,6S,8S,8aS,4'R,6'R,2"S)-6'-{1,2,4a,5, 6,7,8,8a-octahydro-2-methyl-8-[(2"-methyl-1"-oxobutyl)oxy]-6-[(Z)-prop-1-enyl]-1-naphthalenyl)ethyl}-tetrahydro-4'-hydroxy-2H-pyran-2'-one (B) Sodium (1S,2S,4aR,6S,8S,8aS,3'R,5'R,2"S)-7'-(1,2, 4a,5,6,7,8,8a-octahydro-2-methyl-8-[(2"-methyl-1"-oxobutyl)oxy]-6-[(Z)-prop-1-enyl]-1-naphthalenyl)-3', 5'-dihydroxyheptanoate (C) (1S,2S,4aR,6S,8S,8aS,4'R,6'R)-6'-{2-(1,2,4a,5,6,7, 8,8a-octahydro-2-methyl-8-[(2"-dimethyl-1"-oxobutyl)oxy]-6-[(Z)-prop-1-enyl]-1-naphthalenyl)ethyl}-tetrahydro-4'-hydroxy-2H-pyran-2'-one (D) (1S,2S,4aR,6S,8S,8aS,4'R,6'R)-6'-{2-(1,2,4a,5,6, 7,8,8a-octahydro-2-methyl-8-[(2"-dimethyl-1"-oxobutyl)oxy]-6-[(E)-but-1-enyl]-1-naphthalenyl)ethyl}-tetrahydro-4'-hydroxy-2H-pyran-2'-one (E) (1S,2S,4aR,6S,8S,8aS,4'R,6'R,2"S)-6'-{2-(1,2,4a,5, 6,7,8,8a-octahydro-2-methyl-8-[(2"-methyl-1"-oxobutyl)oxy]-6-[(E)-hex-1-enyl]-1-naphthalenyl)ethyl)-tetrahydro-4'-hydroxy-2H-pyran-2'-one (F) (1S,2S,4aR,6S,8S,8aS,4'R,6'R)-6'-{2-(1,2,4a,5,6,7, 8,8a-octahydro-2-methyl-8-[(2"-dimethyl-1"-oxobutyl)oxy]-6-[(E)-hex-1-enyl]-1-naphthalenyl)ethyl}-tetrahydro-4'-hydroxy-2H-pyran-2'-one Particularly preferred compounds of this subgroup are those wherein $R^1$ represents a $C_{4-5}$ branched alkyl group; $R^2$ represents (E)-prop-1-enyl; and $R^5$ represents methyl. Illustrative of this particularly preferred subclass are:

(G) (1S,2S,4aR,6S,8S,8aS,4'R,6'R,2"S)-6'-{2-(1,2,4a,5, 6,7,8,8a-octahydro-2-methyl-8-[(2"-methyl-1"-oxobutyl)oxy]-6-[(E)-prop-1-enyl]-1-naphthalenyl)ethyl}-tetrahydro-4'-hydroxy-2H-pyran-2'-one (H) Methyl (1S,2S,4aR,6S,8S,8aS,3'R,5'R,2"S)-7'-(1,2, 4a,5,6,7,8,8a-octahydro-2-methyl-8-[(2"-methyl-1"-oxobutyl)oxy]-6-[(E)-prop-1-enyl]-1-naphthalenyl)-3',5'-dihydroxyheptanoate (J) Methyl (1S,2S,4aR,6S,8S,8aS,3'R,2"S)-7'-(1,2,4a,5, 6,7,8,8a-octahydro-2-methyl-8-[(2"-methyl-1"-oxobutyl)oxy]-6-[(E)-prop-1-enyl]-1naphthalenyl)-3'-hydroxy-5'-oxoheptanoate (K) (1S,2S,4aR,6S,8S,8aS,4'R,6'R)-6'-{2-(1,2,4a,5,6,7, 8,8a-octahydro-2-methyl-8[(2"-dimethyl-1"-oxobutyl)oxy]-6-[(E)-prop-1-enyl]-1-naphthalenyl)ethyl}-tetrahydro-4'-hydroxy-2H-pyran-2'-one (L) Methyl (1S,2S,4aR,6S,8S,8aS,3'R,5'R)-7'-(1,2,4a,5, 6,7,8,8a-octahydro-2-methyl-8-[(2"-dimethyl-1"-oxobutyl)oxy]-6-[(E)-prop-1-enyl]-1-naphthalenyl)-3',5'-dihydroxyheptanoate (M) Methyl (1S,2S,4aR,6S,8S,8aS,3'R)-7'-(1,2,4a,5, 6,7,8,8a-octahydro-2-methyl-8-[(2"-dimethyl-1"-oxobutyl)oxy]-6-[(E)-prop-1-enyl]-1-naphthalenyl)-3'-hydroxy-4'-oxoheptanoate (N) Sodium (1S,2S,4aR,6S,8S,8aS,3'R,5'R)-7'-(1,2,4a,5, 6,7,8,8a-octahydro-2-methyl-8-[(2"-dimethyl-1"-oxobutyl)oxy]-6-[(E)-prop-1-enyl]-1-naphthalenyl)-3',5'-dihydroxyheptanoate A second preferred subgroup of compounds are those wherein $R^1$ represents a $C_{4-6}$ branched alkyl group; $R^2$ represents a $C_{2-5}$ alkenyl substituted by an optionally substituted phenyl group, each of a and c independently represents a single or double bond; and each of b and d represents a single bond. Illustrative compounds of this subgroup are:

(P) (1S,2S,4aR,6S,8S,8aS,4'R,6'R,2"S)-6'-{2-(1,1,4a,5, 6,7,8,8a-octahydro-2-methyl-8[(2"-methyl-1"-oxobutyl)oxy]-6-[3-phenyl-(E)-prop-1-enyl]-1naphthalenyl)ethyl}-tetrahydro-4'-hydroxy-2H-pyran-2'-one (Q) (1S,2S,4aR,6S,8S,8aS,4'R,6'R)-6'-{2-(1,2,4a,5,6,7, 8,8a-octahydro-2-methyl-8-[(2"-dimethyl-1"-oxobutyl)oxy]-6-[3-phenyl-(E)-prop-1-enyl]-1-naphthalenyl)ethyl}-tetrahydro-4'-hydroxy-2H-pyran-2'-one For simplicity the compounds of Formula II may be subdivided according to the exact form of $R^3$ and Q. Thus the compounds in which Q is the group C=O and $R^3$ is M are considered to be compounds of the subgroup IIe, whereas if $R^3$ is a group of formula $R^4$ the ketones are in the subgroup IIa. Compounds in which Q is the group CHOH and $R^3$ is a group of form $R^4$ make up the subgroup IIb, when $R^3$ is hydrogen the compounds are of subgroup IIc, and when $R^3$ is a group of formula M the compounds are of the subgroup IId.

The present invention also provides novel processes for the preparation of compounds of general formulae I and II as well as certain intermediates in their preparation, as will now be described by reference to the drawings.

Figure 1:
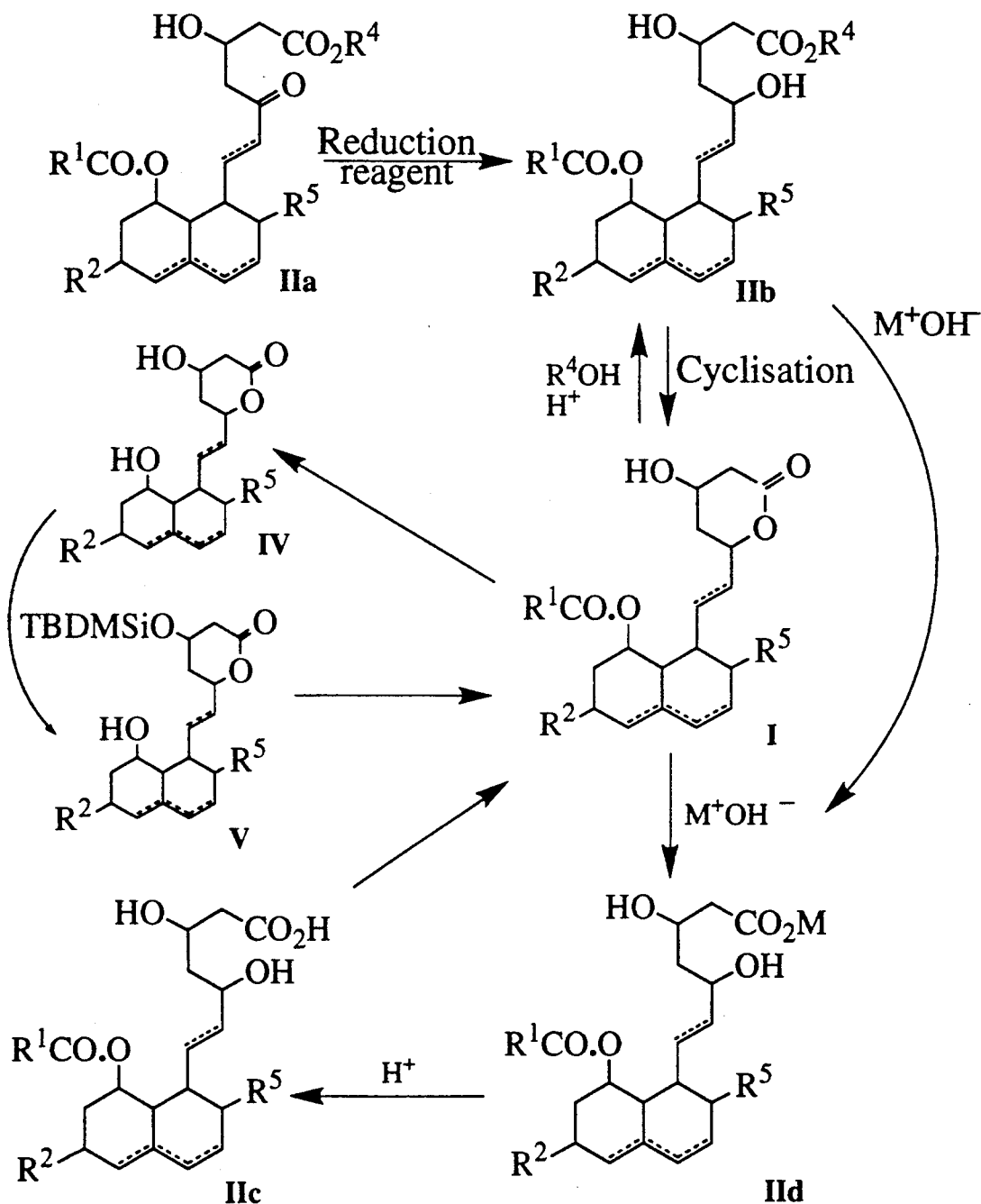
FIG. 1 shows reaction scheme I, which shows the interconversion of compounds of general formula I with subgroups IIa, IIb, IIc and IId and the interconversion of compounds of general formula I with compounds of general formula IV.
Figure 2:
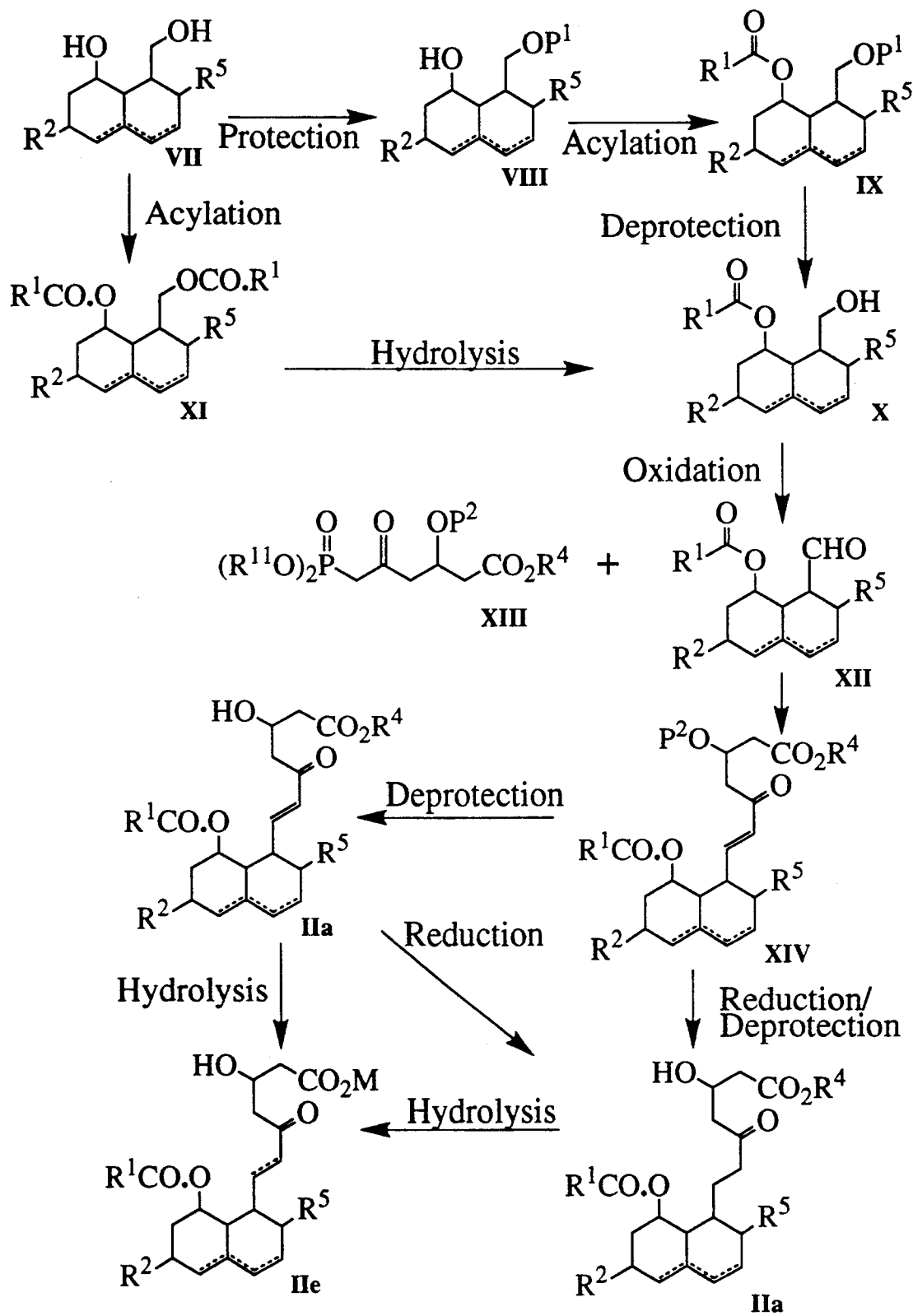
FIG. 2 shows reaction scheme II, which shows a preparative route of compounds of subgroups IIa and IIe from compounds of general formula XIV, which in turn are preparable form compounds of general formula VII.
Figure 3:
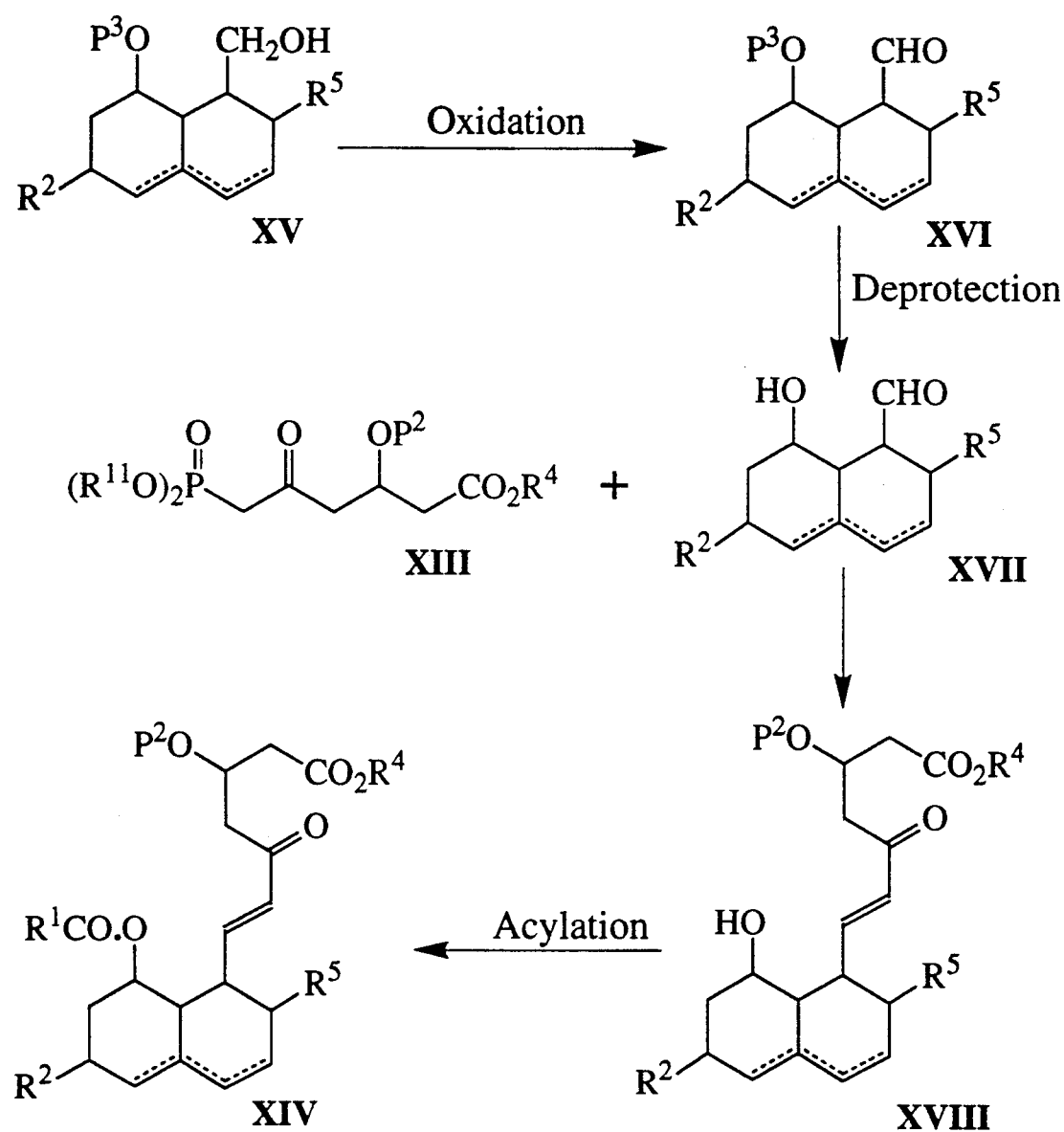
FIG. 3 shows reaction scheme III, which shows a different preparative route of compounds of general formula XIV, this time from compounds of general formula XV.
Figure 4:
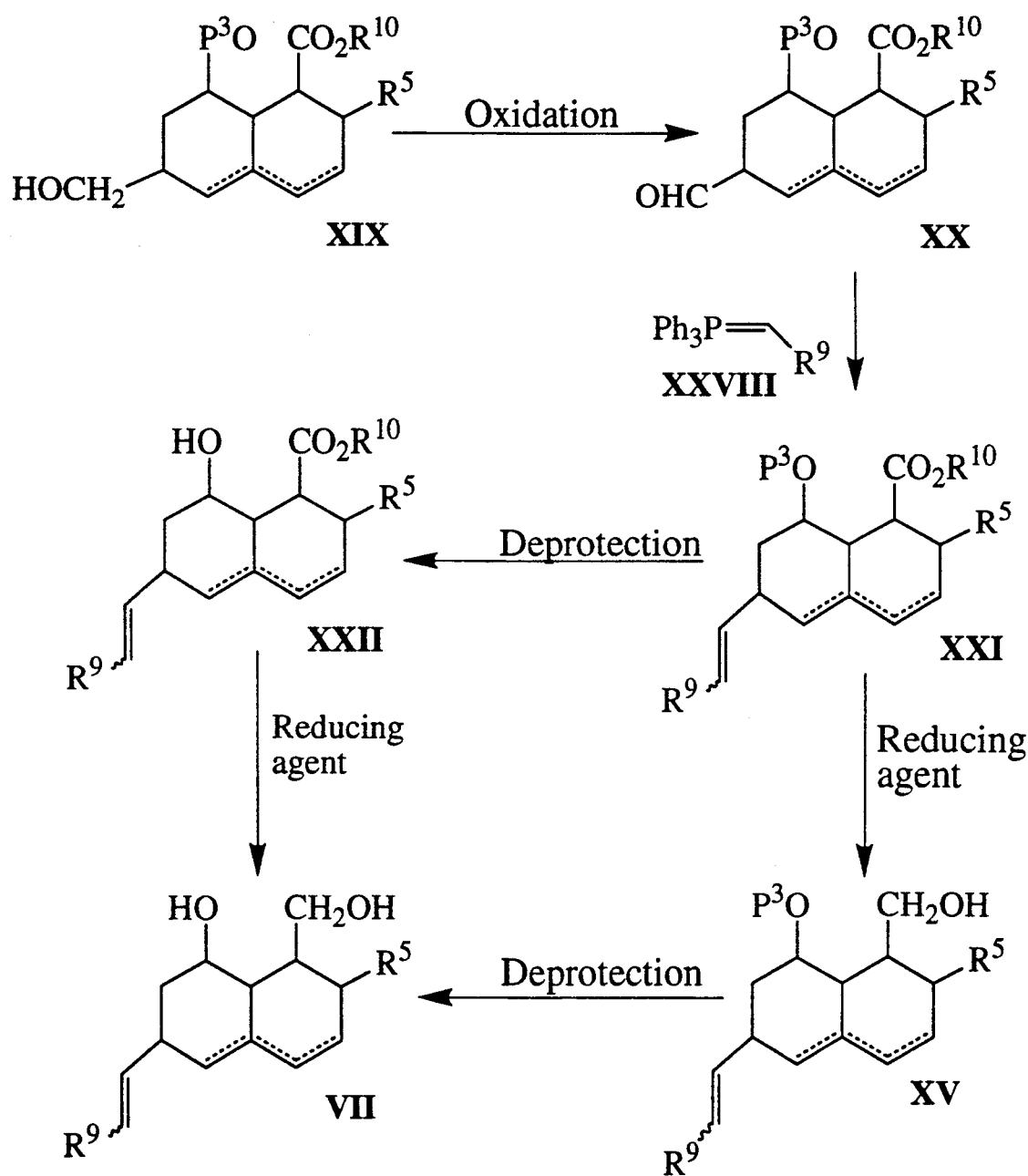
FIG. 4 shows reaction scheme IV, which shows a preparative route of compounds of general formulae VII and XV from compounds of general formulae XXI and/or XXII, which in turn may be prepared from compounds of general formula XIX.
Figure 5:
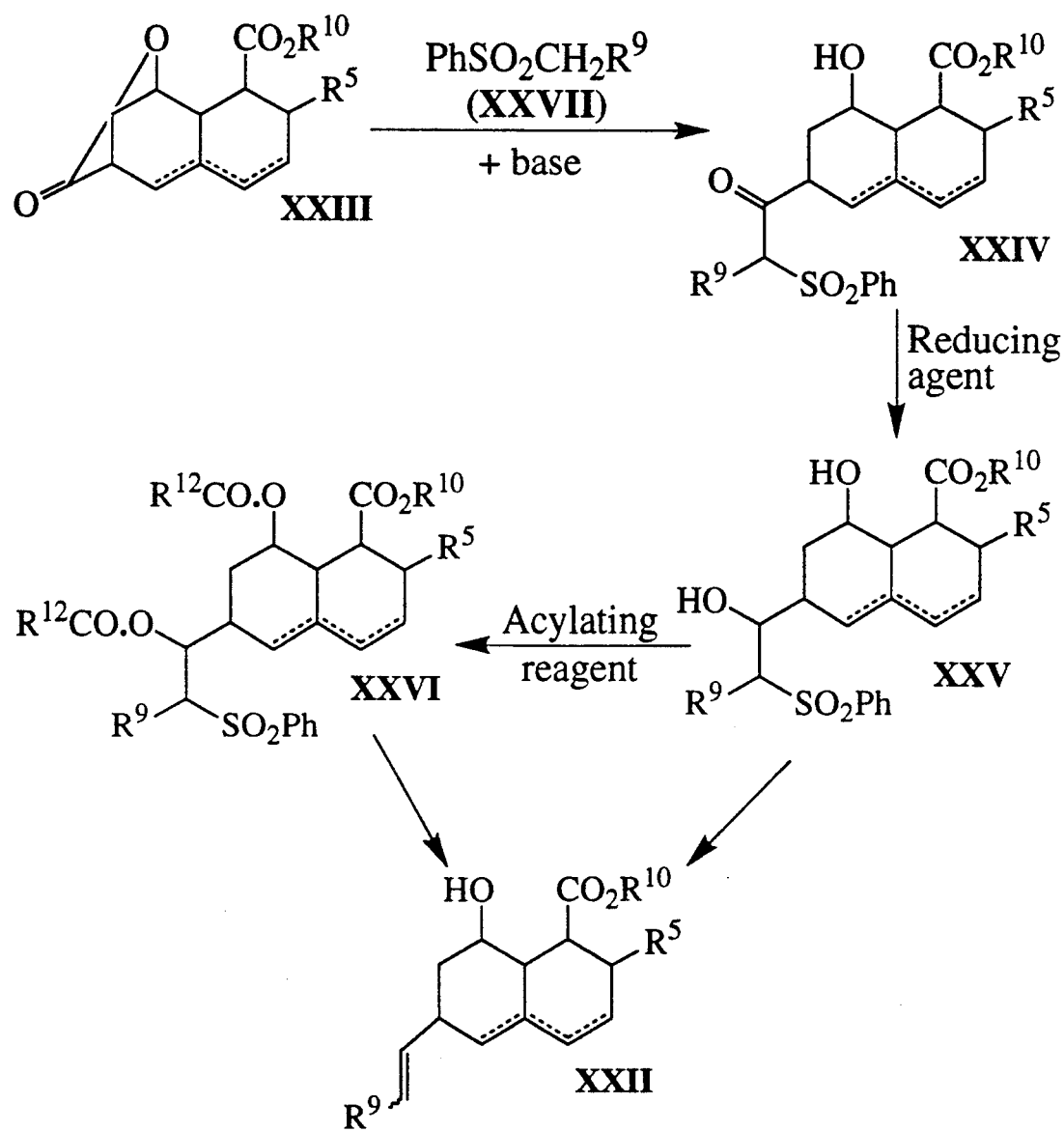
FIG. 5 shows reaction scheme V, which shows a further preparative route for compounds of general formula XXII.
Figure 6:
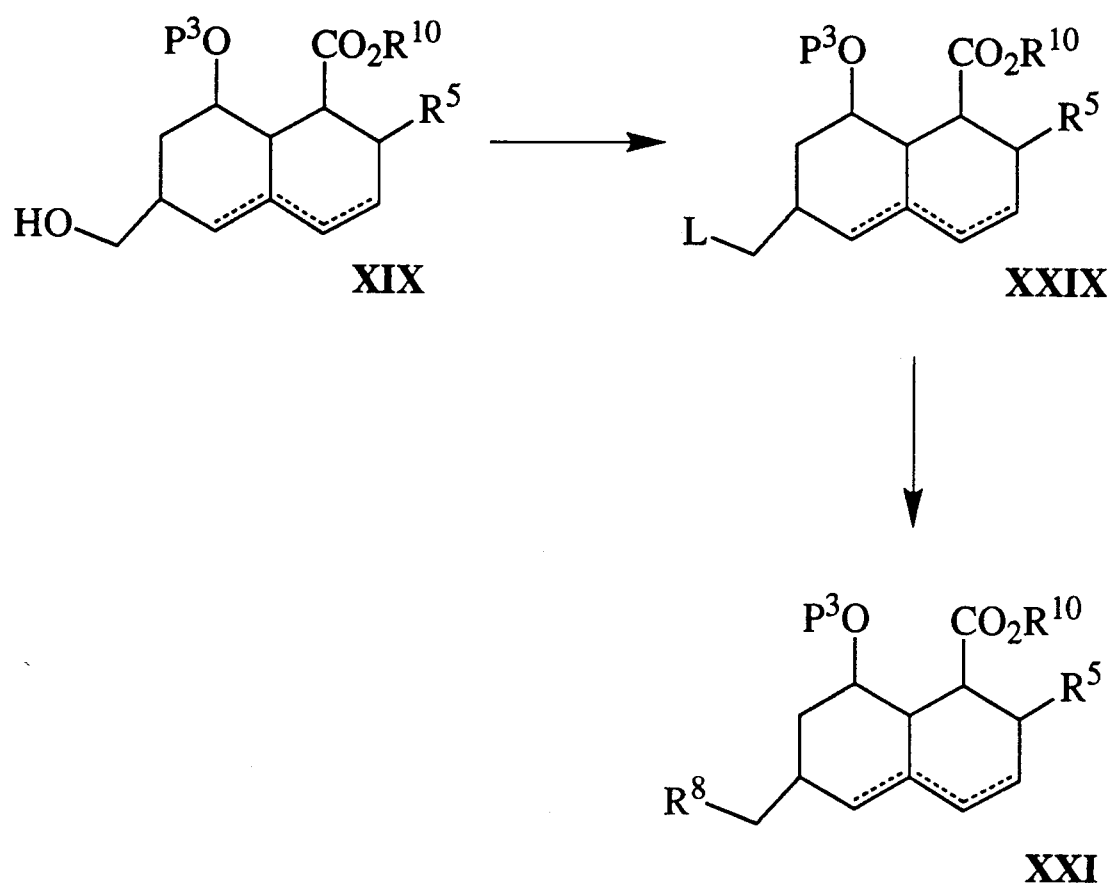
FIG. 6 shows reaction scheme VI, which shows a further preparative route for compounds of general formula XXI.
Figure 7:
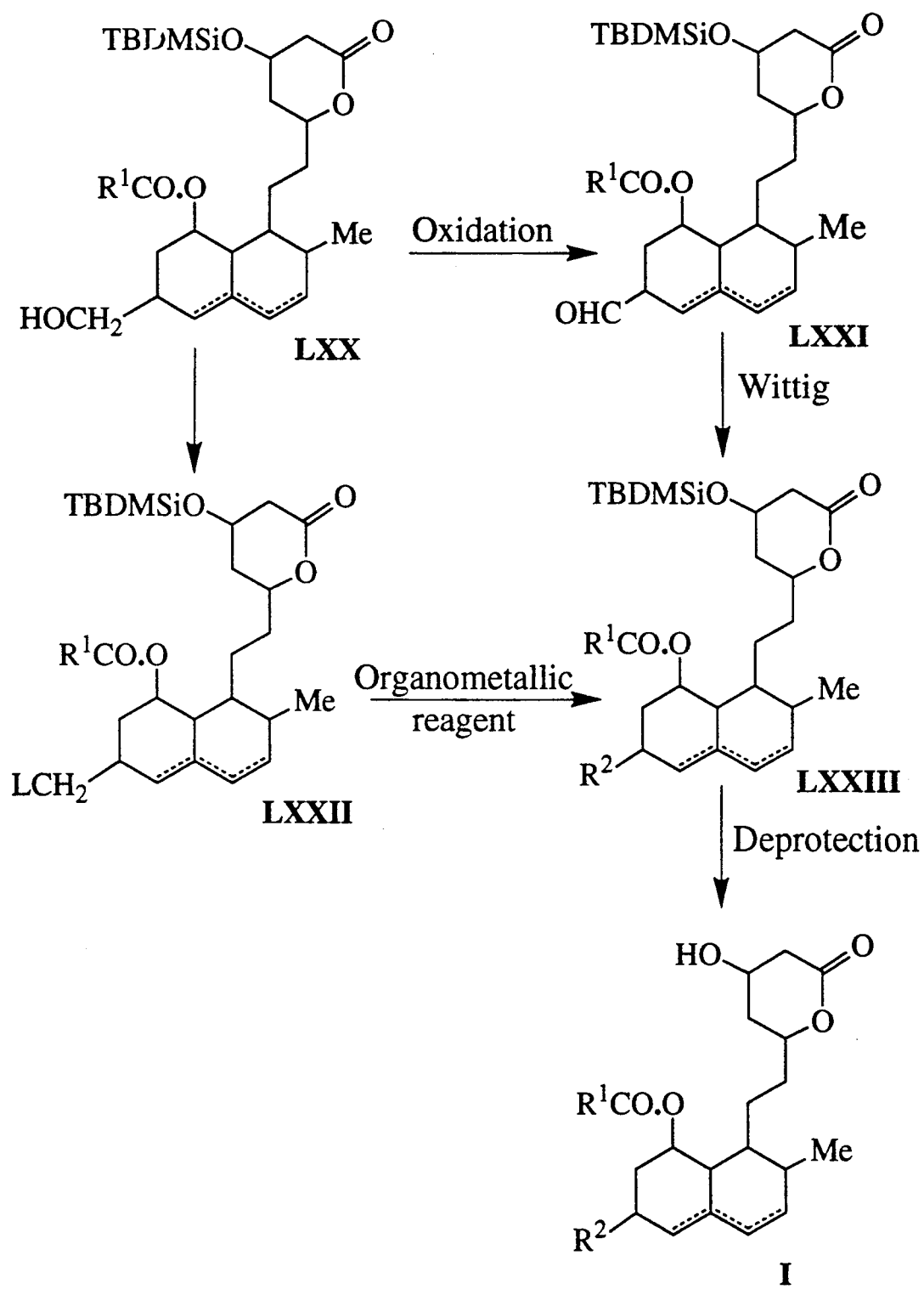
FIG. 7 shows reaction scheme VII, which shows a further route for the preparation of compounds of general formula I.

The compounds of various subgroups IIa-IId of general formula II (hereafter referred to as general formula IIa to IId), and those of general formula I, may be prepared by the general reaction route shown in Scheme I in which $R^1$, $R^2$, $R^4$, $R^5$ and M are as previously defined. Unless the context otherwise requires, substituents in the general formulae in Schemes I and II have the same values as the corresponding substituents in general formulae I and II.

According to a second aspect of the invention, there is provided a process for the preparation of a compound of either of general formulae I and II, the process comprising:

(a) deprotecting and optionally reducing a compound of general formula XIV as shown in Scheme II to form a compound of general formula IIa; or (b) when $R^5$ represents methyl, deprotecting a compound of general formula LXXIII to form a compound of general formula I; and (c) optionally after step (a) or (b) converting a compound of general formula I or IIa directly or indirectly into another compound of general formula I or II.

A ketone of general formula IIa may be reduced to a dihydroxy ester of general formula IIb by redaction of the ketone group with a reducing agent, such as those well known in the art, e.g. sodium borohydride, sodium cyanoborohydride, zinc borohydride, lithium tri-s-butylborohydride or other similar reducing agents that will not reduce the ester functionality. Preferably, the reaction is carried out in such a manner as to maximize the production of the preferred syn isomer of the compound of general formula IIb. The steroselective reduction of compounds of general formula IIa is preferably carried out in two stages, in the first stage the ketone ester is reacted with a trialkylborane, preferably tri-n-butyl borane, or an alkoxydialkylborane, preferably methoxydiethylborane or ethoxydiethylborane (*Chemistry Letters*, 1987, 1923–1926) at ambient temperature in an inert organic solvent such as tetrahydrofuran, diethyl ether, or 1,2-dimethoxyethane, and optionally in the presence of a protic solvent such as methanol or ethanol, and preferably in a mixture of tetrahydrofuran and methanol. The complex which is thus produced is the reduced with sodium borohydride at a temperature between −78° C. and −20° C. The resulting compound of general formula IIb produced from the steroselective reduction contains two asymmetric carbon atoms bearing hydroxyl groups in a syn configuration. Thus reduction of the ketone radical under the conditions described herein produces mostly the syn isomers of compounds of general formula IIb and only a small amount of the less preferred anti isomers.

The ratio of isomers produced will vary according to the specific compound utilized and the reaction conditions employed. Normally, this ratio will be approximately 9:1 to 9.8:02. However, the use of a non-specific reduction method will normally produce a near 1:1 mixture of diastereoisomers. Nevertheless, the mixture of isomers may be separated and purified by conventional techniques and then converted to the compounds of general formula I in a conventional manner well-known to those skilled in the art.

Compounds of general formula IIb may be cyclised to the corresponding lactones of general formula I for example by heating in an inert organic solvent such as benzene, toluene or xylene and azetropically removing the alcohol which is produced. Preferably, the lactonisation is carried out by heating the compound of general formula IIb with an acid, preferably p-toluenesulphonic acid, in benzene or toluene, evaporating the solvent and alcohol thus formed, and repeating the process until all of the compound of general formula IIb has been consumed. If the relative stereochemical configuration of the two carbon atoms bearing the hydroxy groups are established as syn in general formula IIb, then lactonisation will produce the preferred trans lactone of general formula I, otherwise the lactonization will produce a mixture of trans and cis lactones.

A compound of general formula IId may be prepared from a compound of general formula IIb or a compound of general formula I by hydrolysis, preferably hydrolysis with a base such as lithium hydroxide, sodium hydroxide or potassium hydroxide in a mixture of water and an organic solvent such as methanol, ethanol or tetrahydrofuran at a temperature between 0° C. and 50° C. inclusive, preferably at ambient temperature. The cation in compounds of general formula IId is usually determined by the cation of the hydroxide employed; however, the cation may then be exchanged for another cation for example by treatment with ion-exchange resin.

Compounds of general formula IIc may be obtained from compounds of general formula IId by neutralisation, for example careful neutralisation with a mineral acid such as hydrochloric, sulphuric or nitric in aqueous solution, followed by extraction with an appropriate organic solvent. Alternatively, the acids of general formula IIc may be obtained by treating compounds of general formula IId with an ion exchange resin. If the acids of general formula IIc are allowed to stand in solution they slowly re-lactonise to the compounds of general formula I. This process may be accelerated by heating a solution of the acid under conditions that remove the water formed, such as in a Dean-Stark apparatus, or by stirring the solution with a drying agent such as anhydrous sodium sulphate, magnesium sulphate or molecular sieves.

Lactones of general formula I may, if desired, be hydrolysed in the presence of an alcohol and a catalytic amount of acid, preferably p-toluenesulphonic acid, to produce compounds of general formula IIb.

Compounds of general formulae I, IIb, IIc and IId may be converted to compounds of general formula I in which the ester group containing $R^1$ has been exchanged for another ester group, for example via a de-acylated intermediate using the methodology of U.S.

Pat. No. 4,444,784. Thus a compound of general formula I, IIb, IIc or IId may be treated for extended periods, for example 1-3 days, with an alkaline metal hydroxide such as lithium hydroxide, sodium hydroxide or potassium hydroxide in a solvent such as water or an alcohol, and preferably a mixture of water and ethanol, until the ester group containing the group $R^1$ is removed. Mild acid treatment then closes the lactone ring to give an alcohol of general formula IV. The secondary alcohol of general formula IV is then selectively protected with a t-butyldimethylsilyl group under standard conditions to give an intermediate alcohol of general formula V, as shown in Scheme I. Acylation, for example using an acid halide or anhydride in the presence of a mild base such as triethylamine or pyridine, or by using an acid and an activating agent such as carbodiimide and optionally using N,N-dimethylaminopyridine as a catalyst, in an inert solvent such as chloroform, followed by deprotection of the secondary hydroxyl group using tetrabutylammonium fluoride in tetrahydrofuran, buffered with acetic acid, gives a compound of general formula I in which the original group $R^1$ has been exchanged for a different group of formula $R^1$.

A ketone of general formula IIa may be prepared by the methods outlined in Scheme II, in which $R^1$, $R^2$, $R^4$, and $R^5$ are as previously described, and $p^1$, $p^2$ and $R^{11}$ are defined below.

Compounds of Formula IIa wherein d is a double bond may be prepared by removing the protecting group $p^2$ from compounds of formula XIV. This may be achieved in the preferred cases in which $p^2$ is trialkylsilyl or alkyldiarylsilyl by the use of conditions that generate fluoride anions, and preferably by using tetrabutylammonium fluoride in tetrahydrofuran buffered with acetic acid or hydrofluoric acid in aqueous acetonitrile.

Compounds of Formula IIa wherein d is a single bond may be obtained from compounds of Formula IIa wherein d is a double bond by reduction of the carbon-carbon double bond of the enone system, using reagents and conditions that do not affect the other functional groups present. Examples of such reagents are sodium hydrogen telluride, triphenyltin hydride, or tri-n-butyltin hydride with a palladium or platinum catalyst.

Compounds of Formula IIa wherein d is a single bond may also be prepared from enones of general formula XIV by reduction of the double bond followed by deprotection. For example it is possible to reduce the double bond in one reaction by treatment with such mixtures as tri-n-butyltin hydride with a palladium or platinum catalyst, or with a trialkylsilane, preferably triethylsilane, and a catalyst such as tris(triphenylphosphine)rhodium chloride [Wilkinson's catalyst] either neat, using an excess of the silane, or in an inert hydrocarbon solvent such as benzene or toluene at a temperature between ambient and reflux, preferably 50°-70° C. The crude silyl enol ether thus produced is treated with hydrofluoric acid in aqueous acetonitrile to give the compound general formula IIa in which d is a single bond.

However, the preferred method of transformation of compounds of general formula XIV is to treat the enone with a reducing agent, preferably sodium hydrogen telluride in an alcoholic solvent such as methanol or ethanol, and optionally in the presence of a mild buffer such as ammonium chloride, until the starting material is consumed. The protected alcohol thus produced may be purified in the usual way, or used crude, and then the compound may be treated with hydrofluoric acid in aqueous acetonitrile to give the compound general formula IIa in which d is a single bond.

Compounds of general formula IIe may be prepared from compounds of general formula IIa by hydrolysis with a base such as lithium hydroxide, sodium hydroxide or potassium hydroxide in a mixture of water and an organic solvent such as methanol, ethanol or tetrahydrofuran at a temperature between 0° C. and 50° C., preferably ambient temperature. The cation in compounds of general formula IIe is usually determined by the cation of the hydroxide employed; however, the cation may then be exchanged for another cation by treatment with, for example, ion-exchange resins.

Compounds of general formula IIa may be used as intermediates in the production of compounds of general formulae IIb-e and of general formula I as detailed in Scheme I, or they may be used as HMG-CoA reductase inhibitors in their own right.

In compounds of general formulae I and II, the group $R^2$ may be modified to produce different compounds within the general formulae. Among the modifications that can be made are included reducing alkynes to alkenes, reducing alkenes to alkanes, isomerising between E and Z alkenes and/or removing double and/or triple bonds once within the chain.

An enone of general formula XIV may be prepared from an aldehyde of general formula IXX by reaction with a phosphonate of general formula XIII in which $R^{11}$ is a lower (e.g. $C_{1-8}$ or, preferably, $C_{1-4}$) alkyl group such as methyl or ethyl, and the group $P^2$ is any group suitable for the protection of hydroxyl groups, but preferably trialkylsilyl or alkyldiarylsilyl. The reaction between the aldehyde of general formula XII and the phosphonate of general formula XIII may if convenient be carried out in either of the following two ways. In a first method the aldehyde of general formula XII and phosphonate of general formula XIII are reacted together in the presence of a chelating metal halide such as lithium chloride or magnesium bromide and a mild organic base such as triethylamine or 1,8-diazabicyclo[4.5.0]undec-7-ene (DBU) in an inert solvent such as acetonitrile or dimethyl sulphoxide at ambient temperature. In a second method the phosphonate XIII is a first treated with a strong organic base such as lithium diisopropylamide or lithium or sodium bis(trimethylsilyl)amide in an inert organic solvent such as diethyl ether or tetrahydrofuran at a temperature between −78° C. and 0° C., the aldehyde of general formula XII added at the same temperature, and the mixture allowed to warm to ambient temperature, all under an inert atmosphere.

An aldehyde of general formula XII may be prepared from an alcohol of general formula X by oxidation, for example by conventional oxidation reagents such as pyridinium chlorochromate or pyridinium dichromate, or by using a catalytic quantity of tetra-n-propylammonium per-ruthenate and N-methylmorpholine N-oxide, in an inert organic solvent such as dichloromethane or tetrahydrofuran, but preferably the oxidation is carried out using Swern's protocol.

An intermediate alcohol of general formula X may be prepared for example in either of two ways from a diol of general formula VII. In the first method the diol of general formula VII is acylated for example by treatment with an excess of an acid anhydride (($R^1$CO)$_2$O) or acid halide ($R^1$CO.Hal) in the presence of a catalyst such as N,N-dimethylaminopyridine, and a base such as triethylamine or pyridine until both hydroxyl groups in the compound of general formula VII have reacted. The diacylated compound of general formula XI is then hydrolysed for example by treatment with an alkali metal hydroxide such as lithium hydroxide, potassium hydroxide or sodium hydroxide in a solvent such as water or an alcohol, or a mixture of such solvents, at a temperature between 0° C. and ambient for a time suitable to maximise to the production of the alcohol X.

In the second and preferred of the two exemplary methods, the diol of general formula VII is treated under conditions that will selectively protect the primary alcohol, for example either as an ester or an ether. Such conditions are well known to one skilled in the art, but the preferred conditions are to treat with one equivalent of a trialkylsilylchloride or alkyldiarylsilylchloride in the presence of imidazole and, optionally, a mild organic base such as triethylamine or pyridine, and preferably using dichloromethane or chloroform as a solvent. The product of such a reaction will be a compound of general formula VIII wherein $P^1$ is a trialkylsilyl or alkyldiarylsilyl moiety or other protective group. The compound of general formula VIII is then acylated, for example using the conditions described above, that is treatment with the appropriate acid halide ($R^1CO.Hal$) or preferably the anhydride (($R^1CO)_2O$) using a mild organic base such as triethylamine or pyridine and optionally using a catalyst such as N,N-dimethylaminopyridine. The resulting intermediate, a compound of general formula IX, may then be deprotected to give an alcohol of general formula X using such conditions as are appropriate for the removal of the group $P^1$, without affecting the rest of the molecule. For the removal of the preferred trialkylsilyl or alkyldiarylsilyl groups, the preferred methods are to use tetrabutylammonium fluoride in an inert solvent such as tetrahydrofuran, or hydrofluoric acid in aqueous acetonitrile at ambient temperature. However, it will be appreciated by one skilled in the art that other methods are available for the removal of these preferred groups, or that other protecting groups may be used in the transformation of a diol of general formula VII to an alcohol of general formula X.

Intermediate compounds of general formula XIV may also be synthesised from the protected alcohols of general formula XV using the sequence of reactions shown in Scheme III, in which $R^2$, $R^4$, $R^5$, $R^{11}$ and $P^2$ are as previously defined, and $P^3$ is defined below.

An intermediate of general formula XIV may be prepared from an enone of general formula XVIII by acylation, for example using conventional means. Thus, a compound of general formula XIV may be prepared by treating an alcohol of general formula XVIII with an acid chloride or bromide ($R^1CO.Hal$), or preferably an anhydride (($R^1CO)_2O$) in the presence of a mild organic base such as pyridine or triethylamine, and preferably using a catalyst such as N,N-dimethylaminopyridine, either neat or in an inert solvent, preferably dichloromethane or chloroform at a temperature between 0° C. and reflux. Alternatively the transformation may be carried out using the acid ($R^1CO_2H$) and a coupling reagent such as a carbodiimide and a catalyst such as N,N-dimethylaminopyridine, in an inert solvent and preferably at ambient temperature.

An enone of general formula XVIII may be prepared from an aldehyde of general formula XVII and a phosphonate of general formula XIII as defined above for example by using a chelating metal halide such as lithium chloride or magnesium bromide and a mild organic base such as triethylamine or DBU in an inert organic solvent, preferably acetonitrile or dimethylsulphoxide, at a temperature from 0° C. to ambient and preferably under an inert atmosphere.

To prepare an aldehyde of general formula XVII, an alcohol of general formula XV, in which the group $P^3$ is any group suitable for the protection of alcohols, (preferably trialkylsilyl or alkyldiarylsilyl) may be oxidised to an aldehyde of general formula XVI for example by conventional means such as pyridinium chlorochromate or pyridinium dichromate, or by using a catalytic quantity of tetra-n-propylammonium per-ruthenate (TPAP) in the presence of N-methylmorpholine N-oxide in an inert solvent, preferably dichloromethane, but most preferably by using Swern's protocol. The protecting group $P^3$ may then be removed by any appropriate method (but in the preferred case where $P^3$ is trialkylsily or alkyldiarylsilyl, the group may be removed by any method that generates fluoride ions, and preferably using hydrofluoric acid in aqueous acetonitrile, at ambient temperature under an inert atmosphere) to give a hydroxy aldehyde of general formula XVII.

Intermediate alcohols of general formulae VII and XV useful in the syntheses outlined in Schemes II and III may be prepared as shown in Scheme IV, in which $R^2$, $R^5$ and $P^3$ are as previously defined, $R^{10}$ is lower alkyl, and $R^9$ is as defined below.

An intermediate alcohol of general formula XV may be prepared by reduction of the ester group in a compound of general formula XXI, for example using conventional reagents such as lithium aluminum hydride, diisobutylaluminium hydride or lithium triethylborohydride in an inert organic solvent such as diethyl ether or tetrahydrofuran, at ambient temperature to reflux, under an inert atmosphere. The alcohol of general formula XI may be then be used as outlined in Scheme III or may be deprotected to give an alcohol of general formula VII, which may then be used as in Scheme II. The deprotection may be carried out by any means suitable for removal of the group $P^3$, but in the preferred cases in which the group $P^3$ is a trialkylsilyl or alkyldiarylsilyl group, the reaction is preferably carried out using hydrofluoric acid in aqueous acetonitrile, at ambient temperature.

Alternatively, an alcohol of general formula VII may be prepared from an ester of general formula XXI by firstly removing the protecting group $P^3$ and then reducing the ester group in the compound of general formula XXII so formed to the alcohol. The deprotection of a compound of general formula XXI to give a compound of general formula XXII may be carried out in a manner similar to the deprotection of an alcohol of general formula XV, in cases where $P^3$ is one of the preferred groups by treatment with hydrofluoric acid in aqueous acetonitrile, and the reduction of a compound of general formula XXII to a compound of general formula VII may be carried out in a similar manner to the reduction of an ester of general formula XXI to an alcohol of general formula XV by using a (for example conventional) reducing agent in an inert solvent such as diethyl ether or tetrahydrofuran. It is within the capabilities of one of ordinary skill in the art to select the best alternative of those detailed above, according to the exact nature of the groups $R^{10}$ and $P^3$.

An intermediate of general formula XXI may be prepared from an aldehyde of general formula XX by reaction with an ylid of general formula XXVIII in which $R^9$ is $C_{1-6}$ alkyl, $C_{1-6}$ alkenyl, $C_{1-6}$ alkynyl, or $C_{1-3}$ alkyl, alkenyl, or alkynyl substituted with substituted phenyl, in an inert organic solvent, preferably tetrahydrofuran, at a temperature between −78° C. and ambient. It should be appreciated by those skilled in the art that the exact combination of reaction conditions such as solvent, temperature, and reagents used may be varied to produce predominantly one isomer about the newly formed double bond. For example, generation of the ylid by treating ethyl triphenylphosphonium bromide with sodium bis(trimethylsilyl)amide in tetrahydrofuran, at −78° C., then addition of the aldehyde and allowing the mixture to warm to ambient temperature gives a compound in which the newly created alkene is entirely cis —CH=CHMe. However, if the ylid is generated using lithium bis(trimethylsilyl)amide, then a mixture of cis and trans isomers is obtained. This mixture may be carried through the synthetic sequence described above to give a mixture of compound of general formula I or II, or, preferably, separated using standard techniques and the individual components utilised according to the schemes.

An aldehyde of general formula XX may also be used to introduce acetylenic unsaturation into the group $R^2$ in compounds of the invention. For example, any of the following schemes may be appropriate:

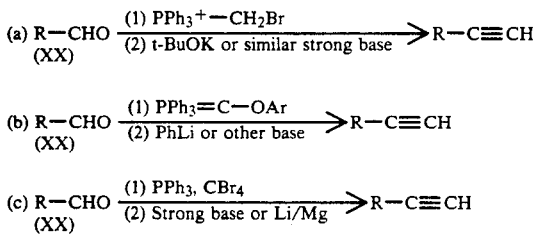

The acetylene R—C≡CH can then be deprotonated and substituted with an appropriate electrophilic radical. Scheme (c) is preferred, using lithium amalgam, as a strong base is not required under these conditions.

Acetylenes may also be produced by reacting a compound of general formula XXII (R—HC=CH—R') with $Br_2/CCl_4$ and then with $NaNH_2$ in $NH_3$ or DMSO to form a compound of the general formula R—HC=CH—R', which may subsequently be used as a compound of general formula XXII, although reaction conditions should be selected appropriately to avoid unwanted effects on the ring double bond.

An aldehyde of general formula XX may be prepared from an alcohol of general formula XIX by oxidation, for example using conventional reagents such as pyridinium dichromate or pyridinium chlorochromate, or by using a catalytic quantity or tetra-n-propylammonium per-ruthenate (TPAP) in the presence of N-methylmorpholine N-oxide, in an inert organic solvent, preferably dichloromethane or chloroform at a temperature between 0° C. and ambient; the transformation is most preferably achieved by using Swern's protocol.

Intermediate esters of general formula XXII may also be produced by the reactions outlined in Scheme V, in which $R^5$, $R^9$, and $R^{10}$ are as defined previously, and $R^{12}$ is defined below.

An alcohol of general formula XXV may be reduced to an intermediate of general formula XXII for example by treatment with sodium amalgam in an alcohol such as methanol or ethanol, and preferably buffered using a phosphate salt such as dipotassium (or disodium) hydrogen phosphate.

Alternatively, an alcohol or general formula XXV may be acylated for example with an acid anhydride $((R^{12}CO)_2O)$ or acyl halide $(R^{12}CO.Hal)$ and a mild organic base such as pyridine or triethylamine, and preferably using N,N-dimethylaminopyridine as a catalyst, in an inert solvent, preferably dichloromethane or chloroform, to give an intermediate ester of general formula XXVI in which $R^{12}$ may be $C_{1-5}$ alkyl, fluorinated $C_{1-5}$ alkyl, or substituted phenyl, but is preferably methyl, ethyl or phenyl. The acylated compound of general formula XXVI may then be transformed to an alcohol of general formula XXII in the same way that a compound of general formula XXV may be transformed as discussed above, that is for example by treatment with sodium amalgam in a buffered alcoholic solvent.

A keto-sulphone of general formula XXIV may be produced from a lactone of general formula XXIII by reaction with an anion or dianion of a sulphone of general formula XXVII, in an inert organic solvent, preferably tetrahydrofuran, at −78° C. to ambient temperature under an inert atmosphere. Reduction of the ketone group in a compound of general formula XXIV, which may be carried out using conventional reagents such as sodium borohydride, cerium borohydride, lithium triethylborohydride, or lithium aluminum hydride in an inert organic solvent from 0° C. to ambient temperature, and preferably using sodium borohydride in methanol or ethanol at ambient temperature, then gives an alcohol of general formula XXV. The alcohol of general formula XXV thus produced is a mixture of diastereoisomers which may be used as a mixture, or separated and used individually.

It will be apparent to one skilled in the art that the exact combination of reaction conditions and reagents used may be varied to produced predominantly one isomer about the newly formed double bond. For example, in the case in which $R^9$ is methyl, elimination of the alcohol of general formula XXV gave material in which the trans:cis ratio about the new double bond was approximately 6:1. It is within the capabilities of one skilled in the art to select conditions, and to choose between the routes outlined in Schemes IV and V, in order to maximise the production of the desired isomer of esters of general formula XXII. Esters of general formula XXII may then be used to produce compounds of general formulae I or II as detailed in Schemes I to III.

Keto-sulphones of general formula XXIV may also be used to introduce acetylenic unsaturation by reaction first with $(EtO)_2P(O)Cl$ and a mild base and then reduction with sodium amalgam to produce the acetylene analogue of a compound of general formula XXII (R—HC=CH—R'). This constitutes a preferred method of synthesis of acetylenes as it avoids the need for a strong base.

Another method of obtaining the intermediate esters of general formula XXI is outlined in Scheme VI in which $R^5$, $R^{10}$, and $P^3$ are as previously defined, and $R^8$ and L are defined below.

An ester of general formula XXI may be obtained by treating an intermediate of general formula XXIX in which L represents a leaving group such as tosyl, mesyl, trifluoromethylsulphonyl, or halide (particularly iodide) with an organometallic reagent that will deliver the group $R^8$ (where $R^8$ is hydrogen, $C_{1-7}$ alkyl, $C_{1-7}$ alkenyl, $C_{1-7}$ alkynyl, or $C_{1-4}$ alkyl, alkenyl, or alkynyl substituted with substituted phenyl) in such a manner that it may be formally represented as a carbanion, in an inert solvent such as diethyl ether or tetrahydrofuran, at a temperature between −78° C. and reflux, under an inert atmosphere.

Examples of suitable organometallic reagents are lithium triethylborohydride, methyl lithium, phenyl lithium, methyl magnesium bromide, lithium acetylide, vinyl lithium, dimethyl copper lithium or other higher order or lower order cooper reagents. The exact form of the organometalic reagent used depends on the form of the leaving grip present in general formula XXIX, and on the other functionality present in the group $R^8$.

Alternatively, in the case where $R^8$ represents hydrogen, the compound of general formula XXI may be obtained from a compound of general formula XXIX in which L represents iodide by treatment with a hydrogen radical source, for example tributyl tin hydride in an inert solvent such as benzene or toluene.

An intermediate of general formula XXIX may be prepared from an alcohol of general formula XIX for example using conventional, well-known procedures.

Compounds of general formula I in which $R^5$ is methyl may also be obtained from known compounds of general formulae LXX and LXXI (EP-A-0251625), using the methods outlined in reaction Scheme VII in which $R^1$, $R^2$, and L are as previously defined.

Lactones of general formula I may be obtained from the protected lactones of general formula LXXIII preferably by treatment with tetrabutylammonium fluoride in tetrahydrofuran buffered with acetic acid at ambient temperature.

A lactone of general formula LXXIII may be obtained by treating an intermediate of general formula LXXII with an organometallic, preferably organocopper, reagent that will deliver the group $R^8$ (as previously defined) in such a manner that it may be formally represented as a carbanion, for example, dimethyl copper lithium or other higher order or lower order copper reagents, in an inert solvent such as diethyl ether or tetrahydrofuran, at a temperature between −78° C. and ambient, under an inert atmosphere. The exact form of the organometalic reagent used depends on the form of the leaving group present in general formula LXXII, and on the other functionality present in the group $R^8$.

An intermediate of the general formula LXXIII may also be prepared from an aldehyde of the general formula aldehyde LXXI by reaction with an ylid of general formula XXVIII, as defined previously, in an inert organic solvent, preferably tetrahydrofuran, at a temperature between −78° C. and ambient. It should be appreciated by those skilled in the art that the exact combination of reaction conditions such as solvent, temperature, and reagents used may be varied to produce predominantly one isomer about the newly formed double bond in the group $R^2$. Any mixture of double bond isomers may be carried through the synthetic sequence to give compounds of general formula I or II, or (preferably) separated using standard techniques and the individual components utilised according to the schemes.

An intermediate of general formula LXXII may be prepared from an alcohol of general formula LXX for example using conventional, well-known procedures.

Intermediates of general formulae XIX and XXIII in which $R^5$ is methyl, $R^{10}$ is ethyl and $P^3$ is a t-butyldimethylsilyl group, a and b are both single bonds and c is a double bond, are known in the literature (J. Chem. Soc., Chem. Commun., 1987, 1986). Those intermediates in which $R^5$, $R^{10}$ and $P^3$ are other groups within the appropriate definitions may be prepared using routes analogous to the known route, but using the appropriately different starting materials. Such a change is within the scope of one skilled in the art. Methods for the introduction of a second double bond at a, isomerising to give a single double bond at a or b, or reducing to give a, b and c as single bonds in compounds with structures similar to the compounds of general formulae I, II, IV, V, VII to XII, XIV to XXIX and LXX to LXXIII are known in the art (for examples, see Tetrahedron 1986, 42, 4909–4951 or U.S. Pat. No. 4,293,496). Some of these methods may use reagents that under certain conditions deleteriously affect at least some of compounds of general formulae I, II, IV, V, VI to XII, XIV to XXIX and LXX to LXXIII; however, other methods may be suitable for the required transformations in some or all of the compounds of general formulae I, II, IV, V, VII or XII, XIV to XXIX and LXX to LXXIII. Thus it is within the capabilities of one skilled in the art to select appropriate methodology for the interconversion of compounds wherein a, b and c may be single or double bonds (subject to the restrictions mentioned in the description), in order to obtain compounds of general formula I or II with the required single or double bonds at a, b or c.

A phosphonate of general formula XIII in which $R^4$ and $R^{11}$ are methyl and $P^2$ is a t-butyldimethylsilyl group is known in the art (J. Org. Chem., 1988, 53, 2374–2378). Compounds of general formulae XXVII and XXVIII are commercially available or are readily available from commercially available materials using known or analogous methods.

In general, reagents are used in sufficient quantities completely to convert starting materials to products but to be themselves substantially consumed during the course of the reaction. However the amounts may often be varied as is evident to one of ordinary skill in the art. For example, in a reaction of two compounds one of which is not readily available and one of which is, an excess of the readily available compound may be used to drive the reaction further towards completion (unless the use of an excess would increase the synthesis of an undesired compound).

Likewise, most of the temperature ranges given in the preceding descriptions are merely exemplary, and it is within the ability of one of ordinary skill int he art to vary those that are not critical.

The reaction times set forth in the preceding description are also merely exemplary and may be varied. As is well-known, the reaction time is often inversely related to the reaction temperature.

Generally, each reaction is monitored, for example by thin layer chromatography, and is terminated when at least one starting material is no longer detectably present, or when it appears that no more of the desired product is being formed.

Conventional work-up procedures have generally been omitted from the preceding descriptions.

As utilised in the preceding descriptions, the term "solvent" embraces mixtures of solvents and implies that the reaction medium is a liquid at the desired reaction temperature. It should, therefore, be understood that not all of the solvents listed for a particular reaction may be utilised for the entire cited temperature range. It should also be understood that the solvent must be at least substantially inert to the reactants employed, intermediates generated and end products under the reaction conditions utilised.

The term "inert atmosphere", as utilised in the preceding descriptions, means an atmosphere that does not react with any of the reactants, intermediates or end products or otherwise interfere with the reaction. While a carbon dioxide atmosphere is suitable for certain reactions, the inert atmosphere is usually nitrogen, helium, neon, or argon, or a mixture thereof, and most often dry argon to maintain anhydrous conditions. Most reactions, including those where the use of an inert atmosphere is not specified, are carried out under an inert atmosphere, usually dry argon, for convenience.

The product of each reaction may, if desired, be purified by conventional techniques such as recyrstalisation (if a solid), column chromatography, preparative thin lay chromatography, gas chromatography (if sufficiently volatile), fractional distillation under high vacuum (if sufficiently volatile) or high pressure (performance) liquid chromatography (HPLC). Often, however, the crude product of one reaction may be employed in the following reaction without purification or even without isolation.

Some reactions, particularly those utilising strong bases or reducing agents, require anhydrous solvents. Where this is the case solvents may be dried before use using conventional techniques and an inert atmosphere used.

Some of the reactions described above may yield mixtures of two or more products, only one of which leads to the desired compound of general formula I or II. Any mixture so obtained may be separated by conventional techniques such as those set forth in the preceding paragraphs.

Certain of the intermediate compounds described above are believed to be noel, in particular compounds of general formulae IV, XIV and LXXIII. All other intermediate comounds in which either or both of $R^2$ and $R^5$ are not methyl are also believed to be novel.

Compounds of this invention are useful as antihypercholesterolaemic agents for the treatment of arteriosclerosis, hyperlipidaemia, familial hypercholesterolaemia and the like diseases in humans.

According to a third aspect of the invention, there is therefore provided a compound of general formula I or II for use in medicine, particularly as antihypercholesterolaemic agents.

According to a fourth aspect of the invention, there is provided the use of a compound of general formula I or II in the preparation of an antihypercholesterolaemic agent. Compounds of the invention can therefore be used in a method for the treatment of prophylaxis of hypercholesterolaemia in general and arteriosclerosis, familial hypercholesterolaemia or hyperlipidaemia in particular comprising administering to a patient an effective dose of a compound of general formula I or II or a mixture thereof.

According to a fifth aspect of the invention, there is provided a pharmaceutical composition comprising a compound of general formula I or II, or a mixture thereof, and a pharmaceutically acceptable carrier therefor. Such a composition may simply be prepared by the admixture of the ingredients.

Compounds of general formula I and II may be administered orally or rectally or parenterally in the form of a capsule, a tablet, an injectable preparation of the like. It is usually desirable to use the oral route. Doses may be varied, depending on the age, severity, body weight and other conditions of human patients but daily dosage for adults is within a range of from about 2 mg to 2000 mg (preferably 5 to 100 mg) which may be given in one to four divided doses. Higher doses may be favourably employed as required.

The compounds of this invention may also be co-administered with pharmaceutically acceptable non-toxic cationic polymers capable of binding bile acids in a non-reabsorbable form in the gastrointestinal tract. Examples of such polymers include cholestyramine, colestipol and poly[methyl-(3-trimethylamino-propyl-)iminotrimethylene dihalide]. The relative amounts of the compounds of this invention and these polymers is between 1:100 and 1:15000.

The intrinsic HMG-CoA reductase inhibition activity of the claimed compounds may be measured in in vitro protocols described in detail in the Examples below.

Included within the scope of this invention is the method of treating arteriosclerosis, familial hypercholesterolaemia or hyperlipidaemia which comprise administering to a subject in need of such treatment a nontoxic therapeutically effective amount of the compounds of Formulae I or II or pharmaceutical compositions thereof.

Compounds of general formula IV may also show HMG-CoA reductase inhibition activity and so may be included in the pharmaceutical aspects of the invention.

The following examples show representative compounds encompassed by this invention and their syntheses. However, it should be understood that they are for the purposes of illustration only.

Organic solutions were dried over sodium sulphate or magnesium sulphate, and evaporated under reduced pressure. NMR spectra were recorded at ambient temperature in deuteriochloroform at 250 MHz for proton and 62.5 MHz for carbon unless noted otherwise. All chemical shifts are given in parts per million relative to tetramethylsilane. Infra red spectra were recorded at ambient temperature in solution in chloroform, or in the solid state in a potassium bromide disc as noted.

Chromatography was carried out using Woelm 32–60 μm silica.

EXAMPLE 1

Compound J

Methyl (1S,2S,4aR,6S,8S,8aS,3′R,2″S)-7′-(1,2,4a,5,6,7,8,8a-octahydro-2-methyl-8-[(2″-methyl-1″-oxobutyl)oxy]-6-[(E)-prop-1-enyl]-1-naphthalenyl)-3′-hydroxy-5′-oxoheptanoate

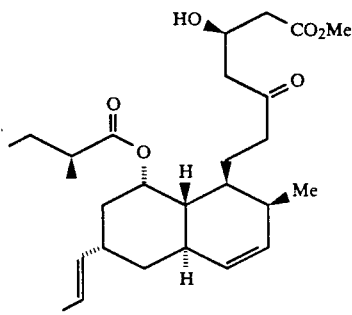

Step 1

Ethyl (1S,2S,4aR,2S,8S,8aS)-1,2,4a,5,6,8, 8a-octahydro-8-hydroxy-6-(1-hydroxy-2-(phenylsulphonyl) propyl)-2-methyl-naphthalene-1carboxylate (XXV)

Ethyl phenylsulphone (General Formula XXVII, $R^9$=methyl; 2.6 g, 15.2 mmol) was dissolved in dry tetrahydrofuran (THF) (100 mL) and cooled to −78° C., under argon. n-Butyl-lithium (1.4 M solution in hexane; 11 mL, 15.4 mmole) was added and stirring continued for 30 minutes at −78° C. A solution of (+) ethyl (1S,2S,4aR,6S,8S,8aS)-1,2,4a,5,6,8, 8a-octahydro-2-methyl-6,8-naphthalene-carbolactone-1-carboxylate (general formula XXIII, $R^5$=methyl; 2.00 g, 7.6 mmole) in dry THF (80 mL) was added to the reaction mixture over 45 minutes, the solution stirred for a further 2 hours, then the reaction quenched by addition of ammonium chloride solution (50 mL). The mixture was warmed to room temperature, poured into either (100 mL), and the remaining solid dissolved using the minimum amount of water. The two phases were separated and the organic phase was washed with ammonium chloride solution (100 mL) and brine (100 mL). The organic solution was dried and evaporated to give a crude oil which was used in the next stage without further purification.

Sodium borohydride (0.15 g, 3.96 mmole) was added to a solution of the crude sulphone addition product in ethanol (100 mL), under argon, the mixture stirred overnight, quenched by the addition of water (100 mL), then extracted into ether (100 mL). The two phases were separated and the organic phase washed with brine (2×100 mL). The combined aqueous solutions were extracted with ether (100 mL), which was then washed with more brine (100 mL). The combined organic solutions were dried and evaporated to an orange oil. Chromatography eluting with 9:1 hexane:ethyl acetate then 4:1 hexane:ethyl acetate gave the pure alcohol (XXV; 1.07 g, 32%) as a colourless oil.

delta H 7.95–7.5 (5H, m), 5.52 (1H, ddd, J 10, 4 and Hz), 5.40 (1H, d, J 10 Hz), 4.57 (1H, dd, J 10 and 1 Hz), 4.0–4.2 (3H, m), 3.49 (1H, dq, J 6 and 1 Hz), 2.7−2.6 (2H, m), 2.28 (1H, br t, J 13 Hz), 2.14 (1H, br d, J 14 Hz), 2.9−2.8 (1H, br m), 1.65−1.6 (3H, m), 1.45 (1H, td, J 111 and 2 Hz), 1.33 (3H, d, J 7 Hz), 1.26 (5H, t, J 7 Hz), and 0.92 (3H, d, J 7 Hz)

Step 2

Ethyl (1S,2S,4aR,6S,8S,8aS)-1,2,4a,5,6,8, 8a-octahydro-8-hydroxy-2-methyl-6-((E)-prop-1-enyl)naphthalene-1-carboxylate (XXII)

Di-sodium hydrogen phosphate (8.6 g, 0.06 mmole) and freshly prepared 6% sodium amalgam (17.25 g) were added to a solution of the alcohol from the previous step (1.07 g, 2.45 mmole) in ethanol (75 mL), under argon, and stirring continued overnight at room temperature. The organics were decanted off and the amalgam and phosphate buffer washed with ether (2×50 mL). The combined organics were washed with water (2×50 mL), dried and evaporated to give a solid which was purified by chromatography using 9:1 hexane:ethyl acetate as eluent to give the olefin (0.12 g, 18%) as an off-white solid.

delta H 5.84 (1H, dd, J 15 and 6 Hz), 5.6−5.5 (2H, m), 5.42 (1H, d, J 10 Hz), 4.29 (1H, m), 4.14 (2H, q, J 7 Hz), 2.84 (1H, dd, J 11 and 6 Hz), 2.7−2.5 (2H, m), 2.40 (1H, br t, J 13 Hz), 2.00 (1H, dq, J 15 and 3 Hz), 1.9−1.7 (2H,m), 1.68 (3H, d, J 6.5 Hz), 1.50 (1H, td, J 13 and 3 Hz), 1.38 (1H, td, J 13 and 5 Hz), 1.26 (3H, t, J 7 Hz), and 0.93 (3H, d, J 7 Hz)

Step 3

(1S,2S,4aR,6S,8S,8aS-1,2,4a,5,6,7,8, 8a-octahydro-8-hydroxy-1-hydroxymethyl-2-methyl-6-((E)-prop-1-enyl)-naphthalene (VII)

A solution of the ester from the previous step (0.60 g, 2.16 mmole) in dry diethyl ether (5 mL) was added dropwise to a stirred suspension of lithium aluminium hydride (0.25 g, 6.48 mmol) in dry diethyl ether (5 mL) under argon. After two hours, the suspension was cooled in an ice bath and water (0.25 mL) was added dropwise, followed by sodium hydroxide solution (15%, 0.25 mL) and water (0.75 mL). The mixture was filtered, the solid washed with diethyl ether and the organics evaporated under reduced pressure to leave the crude diol (0.52 g) as an oil which was used without purification in the next step. delta H 5.93 (1H, ddd, J 14.5, 6.5, and 1.5 Hz), 5.6−5.5 (2H, m), 5.39 (1H, d, J 9.5 Hz), 4.2 (1H, brs), 3.75 (1H, d, J 8.5 Hz), 3.7−3.5 (1H, dd, J 8.5 and 3 Hz), 2.85−2.6 (2H, br m), 2.3−2.6 (3H, br m), 2.1−1.7 (4H, m), 1.68 (3H, dt, J 6.5, and 1 Hz), 1.33 (1H, td, J 13 and 6 Hz),1.22 (1H, td, J 11.5 and 1 Hz), and 0.82 (3H, d, J 6.5 Hz)

Step 4

(1S,2S,4aR,6S,8S,8aS)-1-(t-butyldimethylsilyl)oxymethyl-1,2,4a,5,6,7,8,8a-octahydro-8-hydroxy-2-methyl-6-((E)-prop-1-enyl) naphthalene (VIII)

t-Butyldimethylsilyl chloride (0.358 g, 2.37 mmole) was added in portions to a stirred solution of the diol from the previous step (0.52 g, 2.16 mmole) and imidazole (0.161 g, 2.37 mmole) in dry dichloromethane (5 mL). The mixture was stirred for 18 hours then partitioned between dichloromethane (20 mL) and 1M $H_3PO_4$ (5 mL). The organic phase was separated and washed successively with water (10 mL), saturated sodium bicarbonate solution (10 mL) and brine (7 mL) then dried and evaporate to leave a gum, which was purified by column chromatography eluting with hexane, then hexane:ethyl acetate (9:1) to give the monosilyl ether as a gum (0.62 g, 82%).

delta H (key peaks) 3.55 (1H, t, J 9 Hz, $CH_AH_BOSi$), 3.50 (1H, dd, J 9 and 2.5 Hz, $CH_AH_BOSi$), 0.91 (9H, s, $C(CH_3)_3$), and 0.1 (6H, s, $Si(CH_3)_2$)

Step 5

(1S,2S,4aR,6S,8S,8aS,2'S)-1,2,4a,5,6,7, 8,8a-octahydro-2-methyl-8[(2'-methyl-1'-oxobutyl)oxy]-6-[(E)-prop-1-enyl]naphthalene-1-carbaldehyde (XII)

2(S)-methylbutyric anhydride (1.0 g, 5.37 mmole), dry pyridine (1.3 mL, 16.2 mmole) and 4-dimethylaminopyridine (DMAP; 16 mg, 0.13 mmole) were added to a solution of alcohol from the previous step (0.315 g, 0.9 mmole) in dry dichloromethane (1.5 mL) and the solution heated to 60° C. for 19 hours under argon. The mixture was cooled, diluted with methanol (8.0 mL) and stirred for 1 hour, then partitioned between diethyl ether (80 mL) and 1M $H_3PO_4$ (10 mL). The organic phase was separated and washed successively with $H_3PO_4$ (10 mL), water (10 mL), saturated sodium bicarbonate solution (15 mL) and brine (10 mL), then dried and evaporated to give the acylated product (IX) as a yellow gum, (0.48 g), which was of sufficient purity to proceed directly with the next stage.

delta H (key peaks) 5.0 (1H, m, 8-H), 2.33 (1H, sextet, J 7 Hz, CHCO.O), 1.15 (3H, d, J 7 Hz, $CH_3CH$), 0.9

(3H, t, J 7 Hz, CH₃CH₂), 0.85 (9H, s), 0.1 (3H, s), and −0.1 (3H, s)

A solution of the silylated ester (IX) prepared above (0.48 g, 1.11 mmole) in 40% aqueous HF:acetonitrile (1:19) (8.5 mL) was stirred for half an hour, then saturated sodium bicarbonate solution (10 mL) and diethyl ether (50 mL) added, the aqueous phase separated and further extracted with ether (50 mL). The combined organic layers were washed with brine (20 mL), dried and evaporated to leave the alcohol (X) as a gum, (330 mg), which was used directly in the next stage.

A solution of dry DMSO (0.20 g, 2.55 mmole) in dry dichloromethane (0.8 mL) was added slowly to a cold (−70° C.), stirred solution of oxalyl chloride (0.162 g, 1.27 mmole) in dry dichloromethane (2.0 mL) under an argon atmosphere. After 5 minutes, a solution of the alcohol (X) (0.32 g, 1.03 mmole) in dry dichloromethane (2.0 mL) was added dropwise, stirred for 10 minutes, then a second batch of the DMSO/COCl₂ complex (formed as above; 1.27 mmole) was added dropwise. The solution was stirred for 10 minutes, triethylamine (1.3 mL, 9.26 mmole) added dropwise and the mixture allowed to warm to room temperature. After 1 hour, the mixture was diluted with diethyl ether (50 mL), washed with 1M H₃PO₄ (20 mL), water (3×20 mL), saturated sodium bicarbonate solution (2×20 mL), brine (20 mL) and then dried. Evaporation gave the crude aldehyde which was purified by column chromatography eluting with ethyl acetate:hexane (1:20), giving the aldehyde (XII) (195 mg, 56% from the diol VII).

delta H (key peaks) 9.68 (1H, d, J 2 Hz, CHO), 5.3 (1H, m, 8-H), and 2.65 (1H, m, 1-H)

Step 6

Methyl (1S,2S,4aR,6S,8S,8aS,3'R,2''S)-7'-(1,2,4a,5,6,7,8,8a-octahydro-2-methyl-8-[(2''-methyl-1''-oxobutyl)oxy]-6-[(E)-prop-1-enyl]-1-naphthalenyl)-3'-t-butyldimethylsilyloxy-5'-oxohept-6'-enoate (XIV)

A solution of lithium hexamethyldisilazide in tetrahydrofuran (1.0M, 0.39 mmole) was added dropwise to a cold (−70° C.) stirred solution of methyl 3(R)(t-butyldimethylsilyloxy)-5-oxo-6-(dimethylphosphonyl) hexanoate (general formula XIII; 172 mg, 0.45 mmole) in THF (0.3 mL) under argon. After 1 hour, a solution of aldehyde (XII) (95.4 mg, 0.3 mmole) in THF (0.3 mL) was added, the solution allowed to warm to room temperature and stirred for 64 hours. The reaction was quenched with saturated ammonium chloride solution (5 mL) and extracted with dichloromethane (3×10 mL), which was dried and evaporated to leave a gum. Purification by column chromatography eluting with ethyl acetate:hexane (1:25) to ethyl acetate:hexane (1:20), gave the enone (XIV) (82 mg, 66% based on recovered aldehyde XII).

delta H (key peaks) 6.75 (1H, dd, J 16 and 10 Hz, 7'-H), 5.97 (1H, d, J 16 Hz, 6'-H), 4.59 (1H, quintet, J 6 Hz, 3'-H), 3.64 (3H, s, OCH₃), 2.81 (1H, dd, J 16 and 6 Hz), 2.71 (1H, dd, J 16 and 6 Hz), 2.54 (1H, dd, J 14 and 5 Hz), 2.44 (1H, dd, J 14 and 6 Hz), 0.82 (9H, s), 0.05 (3H, s), and 0.02 (3H, s).

Step 7

Methyl (1S,2S,4aR,6S,8S,8aS,3'R,2''S)-7'-(1,2,4a,5,6,7,8,8a-octahydro-2-methyl-8-[(2''-methyl-1''-oxobutyl)oxy]-6-[(E)-prop-1-enyl]-1-naphthalenyl)-3'-hydroxy-5'-oxoheptanoate (IIa)

A solution of chlorotris(triphenylphosphine) rhodium (I) (2.6 mg, 2.85 micromole) and the enone, (82 mg, 143 mmole) in triethylsilane (2.85 mL, 18.5 mmole) was heated to 50° C. with stirring, under argon, for 1.5 hours. The solvent was evaporated, the residue dissolved in a solution of 40% aqueous hydrofluoric acid in acetonitrile (1:20; 10 mL) and the mixture stirred for 1 hour under argon. Ethyl acetate (20 mL) was added and the organic phase washed with saturated sodium bicarbonate solution (10 mL), which was re-extracted with ethyl acetate (10 mL). The combined ethyl acetate extracts were washed with brine (10 mL), dried and evaporated to leave a gum which was purified by column chromatography eluting with ethyl acetate:hexane (1:4), giving the ketone (45 mg, 69%) as a gum.

delta H 5.72 (1H, dd, J 15 and 8 Hz), 5.6 (1H, m), 5.35 (1H, br d, J 9 Hz), 5.25 (1H, m), 5.15 (1H, m), 4.40 (1H, m), 3.69 (3H, s), 3.39 (1H, br d, J 3 Hz), 2.58 (2H, d, J 5 Hz), 2.48 (2H, d, J 6 Hz), 2.45−1.13 (16H, m), 1.59 (3H, br d, J 6 Hz), 1.11 (3H, d, J 7 Hz), 0.9−0.79 (6H, m)

EXAMPLE 2

Compound H

Methyl(1S,2S,4aR,6S,8S,8aS,3'R,5'R,2''S)-7'-(1,2,4a,5,6,7,8, 8a-octahydro-2-methyl-8-[(2''-methyl-1''-oxobutyl)oxy]-6-[(E)-prop-1-enyl]-1-naphthalenyl)-3',5'-dihydroxyheptanoate

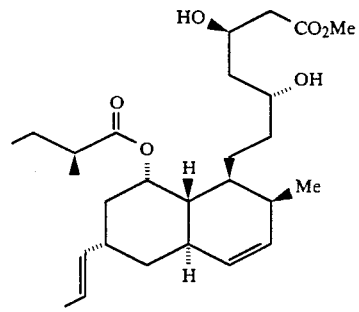

A solution of triethylborane (1.0 M in THF; in 0.1 mmole) was added to a stirred solution of MeOH (0.2 mL) in THF (0.8 mL) under argon. After 45 minutes, 0.22 mL of this mixture was cooled to −70° C., a solution of the ketone of Example 1 (compound J) (8.1 mg, 0.017 mmole) in THF:MeOH (4:1) was added dropwise and stirred a further 1.75 hours. Sodium borohydride (1.0 mg, 0.26 mmole) was added rapidly under argon, the solution stirred for 2.5 hours, then warmed to room temperature and quenched with saturated ammonium chloride solution (0.5 mL). The mixture was stirred for 15 minutes, extracted with ethyl acetate (2×5 mL), dried and evaporated to a gum. Chromatography eluting with hexane:ethyl acetate (3:2) gave the diol as a colourless oil (5.0 mg, 62%).

delta H 0.83 (3H, d, J 7 Hz), 0.91 (3H, t, J 7 Hz), 1.1–2.1 (23H, m), 2.3 (2H, m), 2.5 (3H, d+m, J 7 Hz), 3.27 (1H, br s), 3.71 (3H, s), 3.80 (1H, m), 4.25 (1H, m), 5.20 (1H, m), 5.37 (1H, br d, J 10 Hz), 5.4 (1H, m), 5.65 (1H, ddd, J 10, 5 and 3 Hz), 5.75 (1H, dd, J 14 and 7 Hz)

EXAMPLE 3

Compound G (1S,2S,4aR,6S,8S,8aS,4'R,6'R,2''S)6'-{2-(1,2,4a,5,6,7,8,8a-octahydro-2-methyl-8[(2''-methyl-1''-oxobutyl)oxy]-6-[(E)-prop-1-enyl]-1-naphthalenyl)ethyl}-tetrahydro-4'-hydroxy-2H-pyran-2'-one

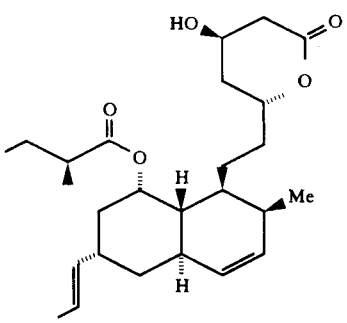

A mixture of the diol of example 2 (compound H) (40 mg) and tosic acid (14 mg, 0.074 mmole) in dry benzene (6 mL) was stirred for half an hour, evaporated, then azeotroped again with benzene (1 mL). The residue was taken up in benzene (5 mL), treated again with tosic acid (14 mg, 0.074 mmole), stirred for half an hour, evaporated under reduced pressure and the residue purified by column chromatography eluting with ethyl acetate:hexane (2:5) to give the lactone as a gum (4.7 mg).

delta H 5.8−5.6 (2H, m), 5.45−5.35 (2H, m), 5.19 (1H, m), 4.65 (1H, m), 4.37 (1H, m), 2.73 (1H, dd, J 17 and 5 Hz), 2.64 (1H, ddd, J 17, 4, and 1 Hz), 2.50 (1H, br m), 2.32 (3H, br m), 2.1−1.2 (18H, m), 1.12 (3H, d, J 7 Hz), and 0.95−0.81 (6H, m)

delta C 176.1, 170.0, 135.9, 132.5, 130.8, 123.0, 76.0, 69.3, 69.2, 62.6, 41.7, 41.6, 38.5, 37.3, 36.0, 35.9, 35.2, 32.9, 31.5, 31.3, 26.6, 23.0, 17.9, 16.3, 14.8, 11.7

EXAMPLE 4

Compound M

Methyl (1S,2S,4aR,6S,8S,8aS,3'R)-7'-(1,2,4a,5,6,7,8,8a-octahydro-2-methyl-8-[(2''-dimethyl-1''-oxobutyl)oxy]-6-[(E)-prop-1-enyl]-1-naphthalenyl)-3'-hydroxy-5'-oxoheptanoate

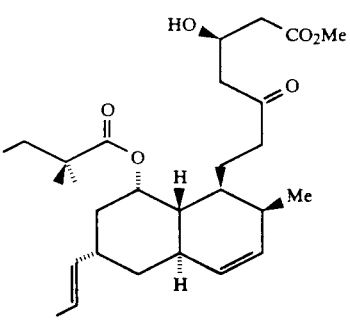

The compound was prepared in the same manner as the compound of Example 1 (compound J) but substituting 2,2-dimethylbutyryl chloride for (S)-2-methylbutyric anhydride in step 5. In addition the procedure of step 7 for the reduction and deprotection of the enone was replaced by the following procedure.

A solution of methyl (1S,2S,4aR,6S,8S,8aS, 3'R)-7'-(1,2,4a,5,6,7,8,8a-octahydro-2-methyl-8-[(2''-dimethyl-1''-oxobutyl)oxy]-6-[(E)-prop-1-enyl]-1-naphthalenyl)-3'-t-butyldimethylsilyloxy-5'-oxohept-6'-enoate (general formula XIV) (66 mg, 0.12 mmol) and ammonium chloride (179 mg, 3.4 mmol) was stirred at room temperature under argon, and sodium hydrogen telluride solution (0.21M in ethanol, 1.6 mL, 0.34 mmol) was added. Further quantities of the telluride were added after 30 minutes (1.4 mL) and 1 hour (0.5 mL). After stirring for a further 20 minutes the solvent was evaporated and the residue partitioned between dichloromethane (50 mL) and saturated ammonium chloride solution (10 mL). The organic layer was dried and the solvent evaporated to leave a clear oil (66 mg).

The oil was taken up in 5 mL of 19.1 acetonitrile:aqueous hydrofluoric acid (40%), the mixture stirred for 45 minutes at room temperature, then diluted with ethyl acetate (25 mL). After washing with saturated aqueous sodium bicarbonate solution (10 mL) and brine (10 mL), the organic solution was dried and evaporated to leave a yellow oil, which was purified by chromatography eluting with hexane:ethyl acetate (9:1 to 4:1) to leave the alcohol as a white solid (49 mg, 88%).

delta H 0.75–0.9 (6H, m), 1.1–1.45 (10H, m), 1.5–1.85 (10H, m), 2.02 (1H, d, J 15 Hz), 2.1–2.3 (2H, m), 2.4–2.5 (3H, m), 2.50 (2H, d, J 6 Hz), 3.38 (1H, d, J 4 Hz), 3.70 (3H, s), 4.43 (1H, m), 5.17 (1H, m), 5.3–5.5 (2H, m), 5.63 (1H, ddd, J 10, 5 and 3 Hz), 5.77 (1H, m)

EXAMPLE 5

Compound L

Methyl (1S,2S,4aR,6S,8S,8aS,3'R,5'R)-7'-(1,2,4a,5,6,7,8,8a-octahydro2-methyl-8-[(2''-dimethyl-1''-oxobutyl)oxy]-6-[(E)-prop-1-enyl]1-naphthalenyl)-3',5'-dihydroxyheptanoate

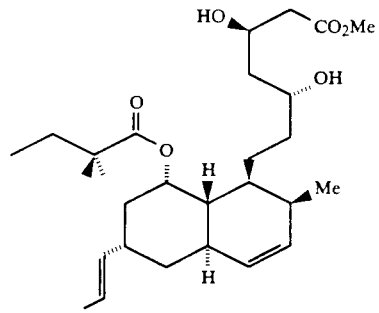

The diol was prepared in the same manner as the diol of Example 2 (compound H) but substituting the ketone of Example 4 (compound M) for the ketone of Example 1.

delta H 0.8–0.9 (6H, m), 1.0–2.0 (24H, m), 2.31 (1H, m), 2.5 (1H, m), 2.50 (2H, d, J 6 Hz), 3.33 (1H, br s), 3.73 (3H, s), 3.76 (1H, br s), 3.8 (1H, m), 4.25 (1H, m), 5.20 (1H, m), 5.38 (1H, d J 9 Hz), 5.4 (1H, m), 5.65 (1H, m), 5.76 (1H, dd, J 12 and 4 Hz)

EXAMPLE 6

Compound K (1S,2S,4aR,6S,8S,8aS,4'R,6'R)-6'-{2-(1,2,4a,5,6,7,8,8a-octahydro-2-methyl-8-[(2''-dimethyl-1''-oxobutyl)oxy]-6-[(E)-prop-1-enyl]-1-naphthalenyl)ethyl}tetrahydro-4'-hydroxy-2H-pyran-2'-one

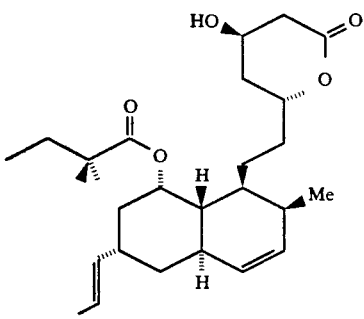

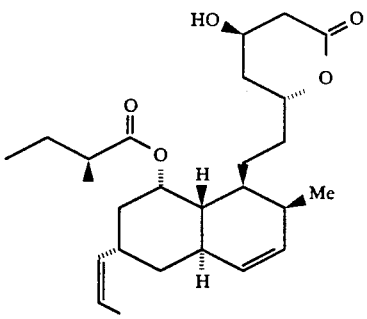

The lactone was prepared in the same manner as the lactone of Example 3 (compound G) but substituting the diol of Example 5 (compound L) for the diol of Example 2.

delta H 0.8 (6H, m), 1.18 (6H, s), 1.2–1.45 (6H, m), 1.5–1.8 (9H, m), 1.85–2.2 (3H, m), 2.31 (1H, m), 2.50 (2H, m), 2.62 (1H, ddd, J 17, 4 and 1 Hz), 2.74 (1H, dd, J 7 and 5 Hz), 4.36 (1H, m), 4.60 (1H, m), 5.18 (1H, m), 5.3–5.45 (2H, m), 5.55–4.85 (2H, m)

delta C 9.2, 14.8, 17.8, 23.1, 24.6, 29.6, 31.2, 31.5, 32.9, 35.2, 36.0, 37.3, 38.5, 41.8, 42.8, 62.6, 69.4, 76.1, 122.8, 130.8, 132.4, 136.0, 170.4, 179.5

EXAMPLE 7

Compound N

Sodium (1S,2S,4aR,6S,8S,8aS,3'R,5'R)-7'-(1,2,4a,5,6,7, 8,8a-octahydro-2-methyl-8-[(2''-dimethyl-1''-oxobutyl)oxy]-6-[(E)-prop-1enyl]-1-naphthalenyl)-3',5'-dihydroxyheptanoate

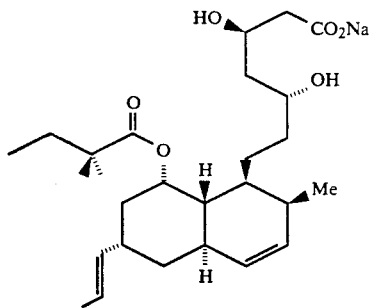

The lactone of Example 6 (compound K) (3.7 mg, 7.6 micromole) was dissolved in 0.068M sodium hydroxide solution in 2:1 methanol:water (125 microL, 8.5 micromole) and left at room temperature for 18 hours. Evaporation of the solvent left the salt as a gum.

EXAMPLE 8

Compound A (1S,2S,4aR,6S,8S,8aS,4'R,6'R,2''S)-6'-{2-(1,2,4a,5,6,7,8,8a-octahydro-2-methyl-8-[(2''-methyl-1''-oxobutyl)oxy]-6-[(Z)-prop-1-enyl]-1-naphthalenyl)ethyl}-tetrahydro-4'-hydroxy-2H-pyran-2'-one

Step 1

(1S,2S,4aR,6S,8S,8aS)-Ethyl 8-(tert-Butyldimethylsilyloxy)-6-formyl-2-methyl-1,2,4a,5,6,7,8,8a-octahydronaphthalene-1-carboxylate (XX)

A solution of dimethylsulphoxide (DMSO) (0.82 ml, 11.6 mmol) in dichloromethane (4 ml) was slowly added to a stirred solution of oxalyl chloride (0.47 ml, 5.4 mmol) in dichloromethane (5 ml) at −60° C. After 5 minutes stirring a solution of (1S,2S,4aR,6S,8S,8a) Ethyl 8-(tert-butyldimethylsilyloxy)-6-hydroxymethyl-2-methyl-1,2,4a,5,6,7,8,8a-octahydronaphthalene-1-carboxylate (general formula XIX) (0.93 g, 2.4 mmol) in dichloromethane (5 ml) was added, and the mixture was stirred a further 30 min. Triethylamine (3.7 ml, 26.5 mmol) was added, the reaction was allowed to warm to room temperature and stirring was then continued for 30 minutes. The mixture was diluted with dichloromethane (25 ml) and washed with aqueous 0.2M hydrochloric acid (20 ml) and saturated aqueous sodium bicarbonate (20 ml). The organic solution was dried (MgSO4) and evaporated in vacuo, leaving a pale yellow oil (1.00 g). This was purified by chromatography (silica; hexane: ether 1:1) to yield the title compound (0.72 g, 77%) as a clear oil.

delta H (C6D6) 0.05 (3H,s) and 0.07 (3H,s) (SiMe2), 1.00 (13H, m 2-Me, t-Bu, 4$_{ax}$-H), 1.07 (3H, t, J 7 Hz, CH2Me), 1.52 (1H, ddd, J 14, 7, and 2 Hz, 7$_{ax}$-H), 1.63 (1H, td, J 12 and 1Hz, 8a-H), 1.80(1H, tt, J 7 and 2 Hz, 6-H), 2.05 (1H, ddt, J 14, 3, and 2Hz, 7$_{eq}$-H), 2.40 (1H, ddt, J 13, 3, and 2 Hz, 5$_{eq}$-H), 2.64 (2H, m, 2-H, 4a-H), 2.92 (1H, dd, J 12 and 6 Hz, 1-H), 4.05 (2H, m, CH2O), 4.58(1H, m, 8-H), 5.49 (2H, m, CH=CH), 9.61 (1H, d, J 1 Hz, CHO)

Step 2

(1S,2S,4aR,6S,8S,8aS)-Ethyl 8-(tert-Butyldimethylsilyloxy)-2-methyl-1,2,4a,5,6,7,8,8a-octahydro-6-((Z)prop-1-enyl)naphalene-1-carboxylate (XXI)

A suspension of ethyltriphenylphosphonium bromide (5.00 g, 13.5 mmol) in THF (17 ml) was stirred at 0° C. under argon while sodium bis(trimethylsilyl)amide in THF (1.0 M; 13.0 ml, 13.0 mmol) was added. The resulting solution was stirred for 15 min and then cooled to −78° C. A solution of the aldehyde from the previous step (0.83 g, 2.2 mmol) in THF (8 ml) was added dropwise and stirring continued cold for 1 hour, and then at room temperature for 17 hours. The mixture was diluted with either (100 ml) and washed with aqueous ammonium chloride (40 ml) and brine (40 ml), then the organic layer was dried (MgSO4) and evaporated in vacuo, leaving a semi-solid (5.3 g). This was purified by chromatography (hexane:ethyl acetate, 50:1) to afford the title compound as a pale yellow oil (0.84 g, 99%).

delta H (CDCl$_3$) −0.09 (3H, s) and 0.00 (3H, s) (SiMe$_2$), 0.86 (d, J 7 Hz, 2-Me) and 0.87 (s,t-Bu) (total 12H), 1.26 (3H, t, J 7 Hz, MeCH$_2$), 1.36 (1H, td, J 13 and 5 Hz, 4$_{ax}$-H), 1.51 (1H, td, J 12 and 2 Hz, 8a-H), 1.58 (dd, J 7 and 1.8 Hz, MeCH=CH) and 1.60 (m, 5$_{eq}$-H)(total 4H), 1.70 (1H, ddd, J 14, 5, and 3 Hz, 7$_{eq}$-H), 1.78 (1H, m, 7$_{ax}$-H), 2.57 (2H, m, 4-H, 2-H), 2.80 (dd, J 12 and 6 Hz, 1-H) and 2.88 (m, 6-H)(total 2H), 4.10 (2H, m, CH$_2$O), 4.36 (1H, m, 8-H), 5.28 (1H, dqd, J 11, 7 and 1.1 Hz, MeCH=CH), 5.37 (1H, br, d, J 10 Hz, 4-H), 5.56 (1H, ddd, J 10,5 and 3 Hz, 3-H), 5.99 (1H, m, MeCH=CH)

Step 3

(1S,2S,4aR,6S,8S,8aS)-1-(tert-Butyldimethylsilyloxy)-8-hydroxymethyl-7-methyl-1,2,3,4,4a,7,8,8a-octahydro-3-((Z)-prop-1-enyl)naphthalene (XV)

The ester from the previous step (0.19 g, 0.48 mmol) was stirred in THF (20 ml) under argon and lithium triethylborohydride in THF (1.0M; 1.0 ml, 1.0 mmol) was added. The mixture was warmed to 80° C. and was stirred at this temperature for 6 hours, fresh portions of lithium triethylborohydride (1.0 ml) being added hourly. The temperature was lowered to 0° C. and water (1 ml) was cautiously added, followed by aqueous 3M sodium hydroxide (2 ml) and 30% aqueous hydrogen peroxide (2 ml). The resulting gel was stirred at room temperature for 2h and then poured onto brine (15 ml) and extracted with ether (2×20 ml). The combined ethereal solutions were dried (MgSO$_4$) and evaporated in vacuo. The residue was purified by chromatography (hexane:ethyl acetate, 25:1) to afford the title compound as a colourless oil (0.12 g, 71%).

delta H 0.07 (3H, s) and 0.08 (3H,s) (SiMe2), 0.91 (9H, s, t-Bu), 0.96 (3H, d, J 7 Hz, 7-Me), 1.00 (1H, s, removed by D$_2$O, OH), 1.13 (1H, td, J 11 and 2 Hz, 8a-H), 1.32 (1H, td, J 13 and 5 Hz, 4$_{ax}$-H), 1.58 (dd, J 7 and 1.9 Hz, MeCH=CH) and 1.6 (m, 2$_{eq}$-H, 4$_{eq}$-H)(total of 5H), 1.79 (1H, ddd, J 14,5 and 1.9 Hz, 2$_{ax}$-H), 2.02 (1H, tt, J 11 and 5 Hz, 8-H), 2.54 (2H, m, 4a-H, 7-H), 2.83 (1H, m, 3-H), 3.49 (1H, td, J 11 and 6 Hz, CHH'OH), 3.90 (1H, m, CHH'OH), 4.01 (1H, m, 1-H), 5.30 (1H, dqd, J 10,7, and 1 Hz, MeCH=CH), 5.36 (1H, br d,J 10 Hz, 5-H), 5.64 (1H, ddd, J 10,5, and 1.6 Hz, 6-H), 5.99 (1H, m, MeCH=CCH)

Step 4

(1S,3S,4aR,6S,8S,8aS)-1-Hydroxy-8-hydroxymethyl-7-methyl-1,2,3,4,4a,7,8,8a-octahydro-3-((Z)-prop-1-enyl)naphthalene (VII)

The alcohol from the previous step (0.54 g, 1.54 mmol) was stirred at room temperature under argon in 19:1 acetonitrile: aqueous hydrofluoric acid (40%) (15 ml) for 15 hours. Ether (150 ml) was added followed by saturated aqueous sodium bicarbonate solution (50 ml). The ethereal solution was dried (MgSO$_4$) and the solvent removed to give the title compound as an off-white solid (0.35 g, 97%). A small sample was recrystallized (dichloromethane/hexane) for analysis.

m.p., 131°-133° C.

nu$_{max}$ (CH$_2$Cl$_2$), 3620,3495 cm$^{-1}$ delta H 0.82 (3H, d, J 7 Hz, 7-Me), 1.30 (1H, td, J 11 and 2 Hz, 8a-H), 1.33 (1H, td, J 13 and 5 Hz, 4$_{ax}$-H), 1.6(m, 4$_{eq}$-H) and 1.63 (dd, J 7 and 1.8 Hz, MeCCH=CH (total of 4H), 1.80 (1H, ddd, J 14,6, and 3 Hz, 4$_{eq}$-H), 1.95 (1H, m, 2$_{ax}$-H), 2.03 (1H, m, 8-H), 2.40 (1H, m, 7-H), 2.41 (1H, br s, removed by D$_2$O, OH), 2.53 (1H, m, 4a-H), 2.76 (1H, br s, removed by D$_2$O, OH'), 2.88 (1H, m, 3-H), 3.65 (1H, dd, J 10 and 1.4 Hz, CHH'OH), 3.76 (1H, t, J 10 Hz, CHH'OH), 4.24 (1H, m, 1-H), 5.37 (1H, br d, J 10 Hz, 5-H), 5.43 (1H, dqd, J 11,7, and 1.4 Hz, MeCH'CH), 5.56 (1H, ddd, J 10,5, and 2.6, 6-H), 6.00 (1H, m, MeCH=CH)

Found: C, 75.93; H, 10.06 Calculated for C$_{15}$H$_{24}$O$_2$: C, 76.22; H, 10.24

Step 5

(1S,3S,4aR,7S,8S,8aS,2'S)-8-Formyl-7-methyl-1,2,3,4, 4a,7,8,8a-octahydro-3-((Z)-prop-1-enyl)-1-naphthalenyl 2'-methylbutyrate (XII)

The title compound was obtained from the diol of step 4 in a similar manner to that in which the diol of Example 1, step 3 was transformed into the aldehyde (Example 1, steps 4 and 5), that is by protection of the primary alcohol, acylation of the secondary alcohol, deprotection of the alcohol, and oxidation.

delta H 0.88(3H, t, J 7 Hz, MeCH$_2$), 0.97 (3H, d, J 7 Hz, 7-Me), 1.13 (3H, d, J 7 Hz, MeCHCO), 1.35-2.05 (7H,m), 1.59 (3H, dd, J 7 and 1.5 Hz, MeCH=CH), 2.30 (1H, sextet, J 7 Hz, MeCHCO$_2$), 2.52 (1H, br t, J 12 Hz, 4a-H), 2.70 (2H, m, 7-H,8-H), 2.91 (1H, m, 3-H), 5.36 (2H, m, 1-H, MeCH=CH), 5.42 (1H, br d, J 10 Hz, 5-H), 5.62 (1H, m, 6-H), 5.79 (1H, br t, J 10 Hz, MeCCH=CH), 9.74 (1H, d, J 2 Hz, CHO)

Step 6

(1R,2S,4aR,6S,8S,8aS,3'R,2''S)-Methyl 3-tert-Butyldimethylsilyloxy-7'-(8-tert-butyldimethylsilyloxy-2-methyl-8-(2''-methylbutyryloxy)-1,2,4a,5,6,7,8,8a-octahydro-6-((Z)-prop-1-enyl)-1-naphthalenyl)-5'-oxohept-6'-enoate (XIV)

The aldehyde from the previous step (91 mg, 0.29 mmol), the keto-phosphonate (general formula XIII) (160 mg, 0.42 mmol) and lithium chloride (18 mg, 0.42 mmol) were stirred at room temperature under argon in acetonitrile (0.22 ml) and 1,8-diazabicyclo[5.4.0]undec-7-ene (0.055 ml, 0.37 mmol) was added. The mixture was stirred at room temperature for 80 hours and then diluted with ethyl acetate (25 ml) and washed with aqueous 0.5M phosphoric acid (10 ml) and brine (10 ml). The combined aqueous layers were extracted with ethyl acetate (25 ml) and the combined organic layers were dried (MgSO$_4$) and evaporated in vacuo. The residue (245 mg) was purified by chromatography (hexane:ethyl acetate, 19:1−9:1), affording the title compound as a colourless oil (32 mg, 20%).

delta H 0.02 (3H,s) and 0.06 (3H,s) (SiMe2), 0.83 (9H, s, t-Bu), 0.85 (3H, t, J 7 Hz, MeCH$_2$), 0.95 (3H, d, J 7 Hz, 2-Me), 1.11 (3H, d, J 7 Hz, MeCHCO), 1.3-2.1 (7H,m), 1.55 (3H, dd, J 7 and 1.5 Hz, MeCH=CH), 2.26 (sextet, J 7 Hz, CHCO$_2$) and 2.31 (m,1-H)(total of 2 H), 2.4-2.7 (4H, m, 4a-H,2-H, and 2'H), 2.75 (2H, m, 4'H), 2.89 (1H, br, 6-H), 3.63 (3H, s, MeO$_2$C), 4,58 (1H, m, 3'-H), 4.88 (1H, m, 8-H), 5.30 (1H, dq, J 11 and 7 Hz, MeCH=CH), 5.42 (1H, br d, J 10 Hz, 4-H), 5.61 (1H, ddd, J 10,5, and 3 Hz, 3-H), 5.74 (1H, m, MeCH=CH), 5.98 (1H, d, J 16 Hz, 6'H), .678 (1H, dd, J 16 and 10 Hz, 7'-H)

The lactone of Example 8 (compound A) (4.7 mg, 11 micromole) was dissolved in 0.067M sodium hydroxide in 2:1 methanol:water (180 microL, 12 micromole) and left at room temperature for 14 hours. Diethyl ether (1 mL) and water (1mL) were added and separated, the aqueous layer washed with a more diethyl ether (1 mL), then evaporated. The residue was taken up in acetone (2 mL), filtered and evaporated to afford the title salt as a glass.

EXAMPLE 10

Compound C (1S,2S,4aR,6S,8S,8aS,4'R,6'R)-6'-{2-(1,2,4a,5,6,7,8,8a-octahydro-2-methyl-8-[(2''-dimethyl-1''-oxobutyl)oxy]-6-[(Z)-prop-1-enyl]-1naphthalenyl)ethyl}-tetrahydro-4'-hydroxy-2H-pyran-2'-one

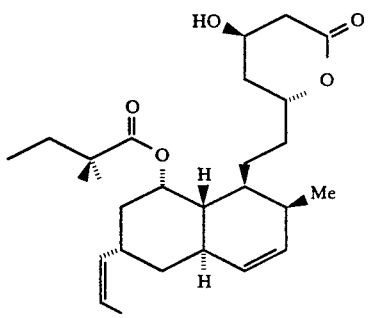

The lactone was prepared in a similar manner to the lactone of Example 8 (compound A) but substituting 2,2-dimethylbutyryl chloride for 2-methylbutyric anhyride in step 5.

Step 7

(1S,2S,4aR,6S,8S,8aS,4'R,6'R,2''S)-6'-{2-(1,2,4a,5,6,7,8,8a-octahydro-2-methyl-8-[(2''-methyl-1''-oxobutyl)oxy]-6-[(Z)-prop-1-enyl]-1-naphthalenyl)ethyl}-tetrahydro-4'-hydroxy-2H-pyran-2'-one (I)

The title compound was obtained from the enone of step 6 in a manner similar to that in which the pyranone of Example 3 (compound G) was obtained from the enone of Example 1, step 6.

delta H 0.86 (3H, d, J 7 Hz, 2-Me) and 0.88 (3H, t, J 7 Hz, MeCH2), 1.11 (3H, d, J 7 Hz, MeCHCO), 1.2–2.4 (17H,m), 1.57 (3H, dd, J 7 and 1.7 Hz, MeCH=CH), 2.51 (1H, br t, 11 Hz, 4a-H), 2.60 (1H, dd, J 18 and 4 Hz, 3'-H), 2.74 (1H dd, J 18 and 5 Hz, 3'-H'), 2.87 (1H, m, 6-H), 4,38 (1H, m, 4'-H), 4.60 (1H, m, 6'-H), 5.20 (1H, m, 8-H), 5.33 (1H, m, MeCH=CH), 5.38 (1H, br d, 4-H), 5.63 (1H, m, 3-H), 5.78 (1H, m, MeCH=CH)

EXAMPLE 9

Compound B

Sodium (1S,2S,4aR,6S,8S,8aS,3'R,5'R,2''S)-7'-(1,2,4a, 5,6,7,8,8a-octahydro-2-methyl-8[(2''-methyl-1''-oxobutyl)oxy]-6-[(Z)-prop-1-enyl]-1-naphthalenyl)-3',5'-dihydroxyheptanoate

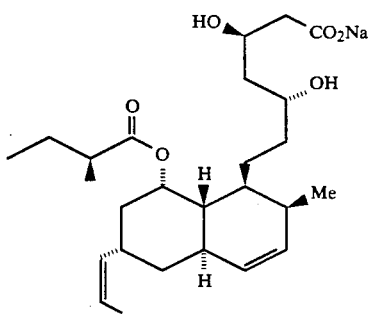

delta H 0.82 (3H, t, J 7 Hz), 0.86 (3H, d, J 7 Hz), 1.14 (6H, s), 1.15–1.45 (6H, m), 1.5–2.1 (12H, m), 2.30 (1H, m), 2.50 (1H, br t, 12 Hz), 2.60 (1H, ddd, J 18, 4 and 1Hz), 2.73 (1H, dd, J 18 and 5 Hz), 2.87 (1H, m), 4.37 (1H, m),4.60 (1H, m), 5.19 (1H, m), 5.2 –5.5 (2, m), 5.65 (1H, m), 5.79 (1H, m)

EXAMPLE 11

Compound D (1S,2S,4aR,6S,8S,8aS,4'R,6'R)-4'-{2-(1,2,4a,5,6,7,8,8a-octahydro-2-methyl-8-[(2''-dimethyl-1''-oxobutyl)oxy]-6-[(E)-but-1-enyl]-1-naphthalenyl)ethyl}-tetrahydro-4'-hydroxy-2H-pyran-2'-one

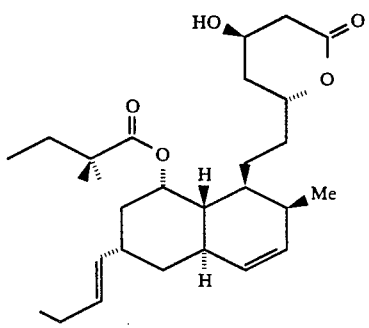

The lactone was prepared in a similar manner to the lactone of Example 6 (compound K) but substituting propyl phenylsulphone in place of ethyl phenylsulphone in the first step.

delta H 5.75 (1H, dd, J 15 and 8 Hz), 5.66 (1H, m), 5.40 (1H, d, J 8 Hz), 5.38 (1H, m), 5.21 (1H, br d, J 2 Hz), 4.60 (1H, br m), 4.37 (1H, quintet, J 3 Hz), 2.74 (1H, dd, J 18 and 5 Hz), 2.61 (1H, ddd, J 18, 4 and 1 Hz), 2.49 (1H, m), 2.31 (1H, m), 2.03–1.57 (12H, m), 1.54–1.15 (12H, m), 0.98–0.80 (9H, m)

delta C 177.4, 170.1, 133.9, 132.4, 130.8, 130.4, 76.1, 69.4, 62.6, 42.9, 41.8, 38.5, 37.5, 37.3, 36.0, 35.3, 32.9, 31.4, 31.2, 29.6, 25.7, 24.6, 23.1, 14.8, 14.3, 14.0

EXAMPLE 12

Compound E (1S,2S,4aR,6S,8S,8aS,4'R,6'R,2''S)-6'-{2-(1,2,4a,5,6,7,8,8a-octahydro-2-methyl-8[(2''-methyl-1''-oxobutyl)oxy]-6-[(E)-hex-1-enyl]-1-naphthalenyl)ethyl}-tetrahydro-4'-hydroxy-2H-pyran-2'-one

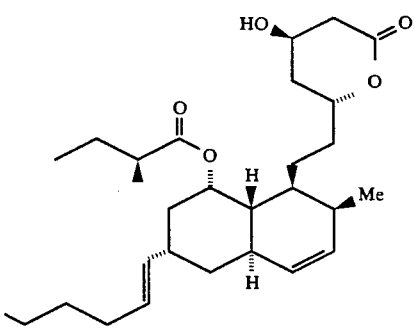

The lactone was prepared in a similar manner to the lactone of Example 6 (compound K) but substituting n-pentyl phenylsulphone in place of ethyl phenylsulphone in the first step, and (S)-2-methylbutyryl anhydride in place of the acid chloride in step 5.

delta H 5.7 (1H, dd, J 14 and 7 Hz), 5.65 (1H, m), 5.4 −53. (2H, m), 5.2 (1H, br d, J 2 Hz), 4.6 (1H, m), 4.35 (1H, quintet, J 3 Hz), 2.8−2.6 (2H, ddd, J 14, 6 and 4 Hz), 2.6−2.2 (5H, m), 2.0−1.2 (17H, m), 1.1 (4H, m+d, J 7 Hz), 0.9−0.8 (9H, m)

delta C 176.3, 170.5, 134.5, 132.5, 130.8, 128.8, 76.2, 69.4, 62.4, 41.6, 38.5, 37.5, 37.3, 35.9, 35.3, 32.8, 32.3, 31.7, 31.5, 31.2, 29.6, 26.6, 23.0, 22.2, 16.2, 14.8, 13.9, 11.6 nu$_{max}$ (neat) 2920, 1720, 1700 cm$^{-1}$

EXAMPLE 13

Compound F (1S,2S,4aR,6S,8S,8aS,4′R,6′R)-6′-{2-(1,2,4a,5,6,7,8,8a-octahydro-2-methyl-8-[(2″-dimethyl-1″-oxobutyl)ocy]-6-[(E)-hex-1-enyl]-1-naphthalenyl)ethyl}-tetrahydro-4′-hydroxy-2H-pyran-2′-one

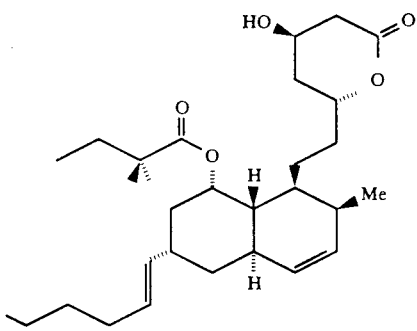

The lactone was prepared in a similar manner to the lactone of Example 6 (compound K) but substituting pentyl phenylsulphone in place of ethyl phenylsulphone in the first step.

delta H 5.76 (1H, dd, J 15 and 8 Hz), 5.66 (1H, ddd, J 10, 5 and 3 Hz), 5.42−4.30 (2H, m), 5.21 (1H, m), 4.61 (1H, m), 4.38 (1H, m), 2.78 (1H, dd, J 17 and 5 Hz), 2.62 (1H, dd, J 17 and 4 Hz), 2.52−1.22 (23H, m), 1.16 (3H, s), 1.15 (3H, s), 0.98−0.80 (9H, m)

delta C 177.4, 170.0, 134.7, 132.4, 130.8, 128.9, 76.1, 69.4, 62.6, 42.9, 41.8, 41.7, 38.5, 37.6, 37.3, 36.0, 35.3, 32.9, 32.3, 31.8, 31.5, 31.2, 29.6, 26.6, 24.9, 23.1, 14.8, 13.9, 9.2, 9.2

EXAMPLE 14

Compound P (1S,2S,4aR,6S,8S,8aS,4′R,6′R,2″S)-6′-{2-(1,2,4a,5,6,7,8,8a-octahydro-2-methyl-8[(2″-methyl-1″-oxobutyl)oxy]-6-[3-henyl-(E)-prop-1-enyl]-1-naphthalenyl)ethyl}-tetrahydro-4′-hydroxy-2H-pyran-2′-one

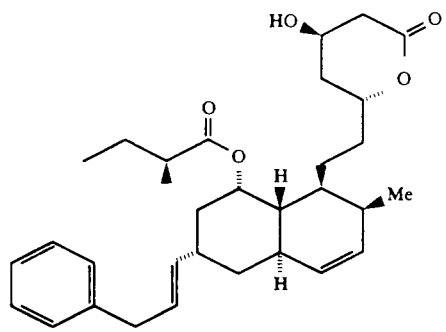

The lactone was prepared in a similar manner to the lactone of Example 6 (compound K) but substituting 2-phenylethyl phenylsulphone in place of ethyl phenylsulphone in the first step, and (S)-2-methylbutyryl anhydride in place of the acid chloride in step 5.

delta H 7.31−7.14 (5H, m), 5.88 (1H, dd, J 15 and 8 Hz, 5.68 (1H, m), 5.56 (1H, dr, J 15 and 7 Hz), 5.41 (1H, m), 5.25 (1H, s), 4.38 (1H, m), 3.32 (2H, br d, J 7 Hz), 2.75 (1H, dd, J 17 and 5 Hz), 2.67−1.16 (21H, m), 1.12 (3H, d, J 7 Hz), 0.92−0.85 (6H, m)

delta C 176.2, 170.1, 140.7, 136.3, 134.6, 132.5, 130.7, 128.3, 128.2, 127.2, 125.6, 76.0, 69.3, 62.6, 41.7, 41.5, 38.9, 38.5, 37.5, 37.3, 36.0, 35.8, 35.3, 32.6, 31.5, 31.2, 26.6, 23.0, 16.2, 14.8, 11.6

EXAMPLE 15

Compound O (1S,2S,4aR,6S,8S,8aS,4′R,6′R)-6′-{2-(1,2,4a,5,6,7,8,8a-octahydro-2-methyl-8[(2″-dimethyl-1″-oxobutyl)oxy]-6-[3-phenyl-(E)-prop-1-enyl]-1naphthalenyl)ethyl} tetrahydro-4′-hydroxy-2H-pyran-2′-one

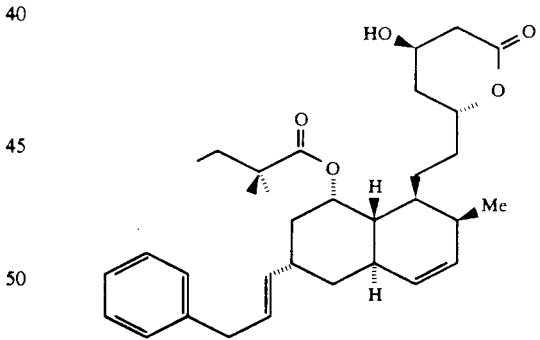

The lactone was prepared in a similar manner to the lactone of Example 6 (compound K) but substituting 2-phenylethyl phenylsulphone in place of ethyl phenylsulphone in the first step.

delta H 7.32−7.15 (5H, m), 5.94 (1H, dd, J 15 and 8 Hz), 5.66 (1H, ddd, J 10, 5 and 3 Hz), 6.63 (1H, dt, J 15 and 7 Hz), 5.40 (1H, br d, J 10 Hz), 5.23 (1H, m), 4.61 (1H, m), 4.38 (1H, m), 3.32 (2H, br d, J 7 Hz), 2.75 (1H, dd, J 18 and 5 Hz), 2.62 (1H, ddd, J 18, 4 and 1 Hz), 2.64−1.2 (18H, m), 1.16 (6H,s), 0.88−0.82 (6H, m)

delta C 177.4, 170.0, 140.8, 136.5, 135.0, 132.5, 130.7, 128.3, 128.2, 127.1, 125.7, 76.1, 69.4, 62.7, 42.9, 41.8, 38.9, 38.5, 37.5, 37.3, 36.0, 35.9, 35.4, 33.2, 32.9, 31.5, 31.2, 29.7, 23.1, 14.8, 9.2

EXAMPLE 16

Compound R (1S,4aR,6S,8S,8aS,4′R,6′R,2″S)-6′-{2-(1,2,4a,5,6,7,8,8a-octahydro-8-[(2″-methyl-1″-oxobutyl)oxy]-6-methyl-1naphthalenyl)ethyl}tetrahydro-4′-hydroxy-2H-pyran-2′-one

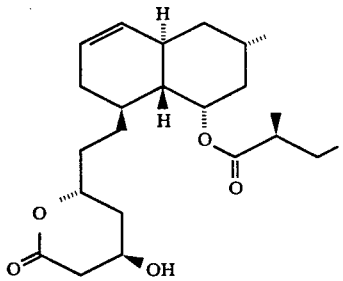

The intermediate alcohol (1S,4aR,6S,8S,8aS)-1,2,4a,5,6,7,8,8a-octahydro-8-hydroxy-1-hydroxymethyl-2-methylnaphthalene (general formula XXIII, $R^5$=hydrogen, $R^{10}$=ethyl) was prepared according to the literature method (A. H. Davidson, C. D. Floyd, A. J. Jones, C. N. Lewis, and P. L. Myers, *J. Chem. Soc., Chem. Commun.*, 1987, 1786) but substituting penta-2,4-dienyl bromide for hexa-2,4-dienyl bromide. This was then transformed into the lactone in a manner similar to that used for the synthesis of the lactone of Example 6 (compound K) but substituting (S)-methyl butyric anhydride for dimethylbutyryl chloride.

delta H 5.65 (1H, m), 5.44 (1H, br d, J 10 Hz), 5.30 (1H, m), 4.62 (1H, m), 4.37 (1H, m), 2.75 (1H, dd, J 17 and 5 Hz), 2.62 (1H, ddd, J 17, 4 and 1 Hz), 2.75 −1.2 (20H, m), 1.16−1.10 (6H, m), 0.94−0.88 (3H, t, J 7 Hz)

delta C 176.2, 170.1, 132.4, 125.5, 76.0, 69.0, 65.8, 62.8, 47.2, 38.6, 38.5, 35.9, 35.6, 33.7, 32.4, 31.8, 29.7, 27.0, 26.6, 20.9, 16.4, 15.2, 11.7

EXAMPLE 17

Compound S (1S,2S,4aR,6S,8S,8aS,4′R,6′R)-6′-{2-(1,2,4a,5,6,7,8,8a-octahydro-2-methyl-8-(acetoxy)-6-[(Z)-prop-1-enyl]-1-naphthalenyl)ethyl}-tetrahydro-4′-hydroxy-2H-pyran-2′-one

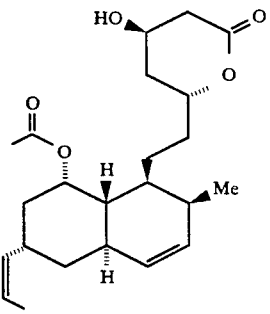

The lactone was prepared in a similar manner to the lactone of Example 8 (compound A) but substituting acetic anhydride in place of 2-methylbutyric anhydride in step 5.

delta H 0.85 (1H, d, J 7 Hz), 1.2–2.2 (16H, m), 2.03 (3H, s), 2.30 (1H, m), 2.52 (1H, br, t, J 12 Hz), 2.62 (1H, ddd, J 18, 4 and 1 Hz), 2.75 (1H, dd, J 18 and 5 Hz), 2.88 (1H, m), 4.38 (1H), m), 4.66 (1H, m), 5.17 (1H, m), 5.35 (1H, m), 5.38 (1H, br d, J 10 Hz), 5.67 (1H, dd, J 10, 5 and 2 Hz), 5.76 (1H, br t, J 10 Hz)

EXAMPLE 18

Compound T (1S,2S,4aR,6S,8S,8aS,4′R,6′R)-6′-{2-(1,2,4a,5,6,7,8,8a-octahydro-2-methyl-8[(2″-dimethyl-1″-oxobutyl)oxy]-6-[3-methyl-(E)-but-1-enyl]-1-naphthalenyl)ethyl)-tetrahydro-4′-hydroxy-2H-pyran-2′-one

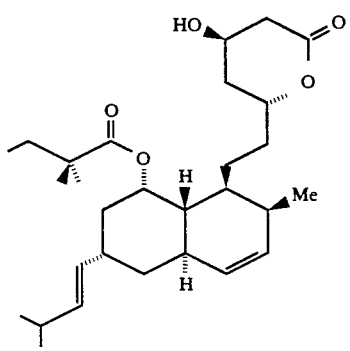

The lactone was prepared in a similar manner to the lactone of Example 6 (compound K) but substituting (2-methylpropyl) phenylsulphone in place of ethyl phenylsulphone in the first step.

delta H 5.72 (1H, dd, J 15 and 9 Hz), 5.65 (1H, m), 5.40 (1H, br d, J 10 Hz), 5.30 (1H, dd, J 15 and 7 Hz), 5.24 (1H, m), 4.62 (1H, m), 4.39 (1H, quintet, J 3 Hz), 2.75 (1H, dd, J 17 and 5 Hz), 2.61 (1H, ddd, J 17, 3 and 1 Hz), 2.48−1.16 (25H, m), 0.98−0.82 (12H, m)

delta C 174.0, 170.1, 136.4, 132.6, 131.9, 131.0, 76.1, 69.6, 62.8, 43.0, 42.1, 38.6, 38.1, 37.3, 35.7, 35.4, 35.3, 33.0, 31.4, 29.7, 24.8, 23.5, 23.0, 15.1, 9.6

EXAMPLE 19

Compound U (1R,2S,4aR,6S,8S,8aS,4′R,6′R)-6′-{2-(1,2,4a,5,6,7,8,8a-octahydro-2-methyl-8-[(2″-dimethyl-1″-oxobutyl)oxy]-6-[(E)-prop-1-enyl]-1-naphthalenyl)-(E)-ethenyl}-tetrahydro-4′-hydroxy2H-pyran-2′-one

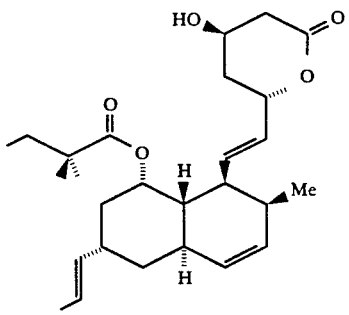

The lactone was prepared in a similar manner to the lactone of Example 6 (compound K) but but omitting the reduction with sodium hydrogen telluride, in step 7.

delta H 5.8−5.6 (3H, m), 5.5−5.3 (3H, m), 5.15 (1H, ddd, J 12, 7 and 3 Hz), 5.0 (1H, d, J 2 Hz), 4.37 (1H, m), 2.74 (1H, dd, J 17 and 5 Hz), 2.62 (1H, ddd, J 17, 4 and 1 Hz), 2.6−2.1 (4H, m), 2.0−1.5 (9H, m), 1.4−1.2 (3H, m), 1.17 (3H, s), 1.13 (3H, s), 0.92 (3H, d, J 7 Hz), 0.85 (3H, t, J 7 Hz)

delta C 177.2, 170.1, 136.3, 135.9, 132.6, 130.6, 129.6, 132.1, 76.9, 70.3, 62.8, 42.0, 41.6, 38.5, 37.4, 36.8, 36.3, 35.7, 35.6, 32.9, 30.7. 24.8, 24.7, 18.0, 16.5, 9.2

EXAMPLE 20

Compound W (1S,2S,4aR,6S,8S,8aS,4′R,6″R,2″ S)-6′-{2-(1,2,4a,5,6,7,8,8a-octahydro-2-methyl-8-[(2″-methyl-1″-oxobutyl)oxy]-6-propyl-1-naphthalenyl)ethyl}-tetrahydro-4′-hydroxy-2H-pyran-2′-one

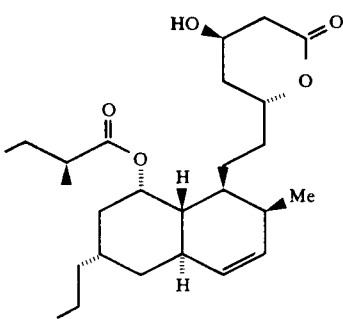

The lactone was isolated as a side product in the synthesis of compound G (Example 3) and was purified by chromatography on C-18 reverse phase silica, eluting with methanol:water (7:3).

delta H 0.85 (3H, d, J 7 Hz), 0.87 (3H, t, J 7 Hz), 0.91 (3H, t, J 7 Hz), 1.13 (3H, d, J 7 Hz), 1.2–2.6 (23H, m), 2.58 (1H, ddd, J 18, 4, and 2 Hz), 2.74 (1H, dd, J 18 and 5 Hz), 4.38 (1H, m), 4.60 (1H, m), 5.18 (1H, m), 5.38 (1H, br d, J 10 Hz), 5.64 (1H, ddd, J 10, 5 and 2 Hz)

EXAMPLE 21

Pharmacology

IN VITRO DETERMINATION OF INHIBITORY POTENTIAL OF HMG-CoA REDUCTASE INHIBITORS

HMG-CoA reductase was induced in rats by feeding a normal diet supplemented with 3% cholestyramine resin for one week prior to sacrifice. The livers were excised from the sacrificed rats and microsomal pellets prepared by the method of Kleinsek et al, Proc. Natl. Acad. Sci. USA, 74 (4), pp 1431–1435, 1977. Briefly, the livers were immediately placed in ice-cold buffer I (see below) and homogenised in a Potter-Elvehjem type glass/TEFLON homogeniser (10 passes at 1000 rpm). (The word TEFLON is a trade mark for p.t.f.e.) The homogenate was centrifuged twice at 20,000×g to remove debris. The supernatant was centrifuged at 100,000×g for 75 minutes, the microsomal pellet resuspended in buffer II (see below) and centrifuged at 100,000×g for 75 minutes. The resultant pellet was stored at −70° C. until required for assay purposes.

| Buffer I | Buffer II |
| --- | --- |
| 50 mM KPO$_4$ pH 7.0 | 50 mM KPO$_4$ pH 7.0 |
| 0.2 M sucrose | 0.2 M sucrose |
| 2 mM DTT | 2 mM DTT |
|  | 50 mM EDTA |

Assay of HMG-CoA Reductase Activity and Determination of Activity of Inhibitors

Membrane bound enzyme isolated as above is used for determining the activity of inhibitors. The assay is performed in a total volume of 300 μl in 100 mM KPO$_4$ pH 7.2 buffer, containing 3 mM MgCl$_2$, 5 mM glucose-6-phosphate, 10 mM reduced glutathione, 1mM NADP, 1 unit glucose-6-phosphate dehydrogenase, and 1 mg/ml BSA, with resuspended enzyme. Putative inhibitors are converted to sodium salts, then dissolved in dimethylsulphoxide and 10 μl aliquots added to the incubation.

The assay is pre-incubated at 37° C. for 10 minutes and initiated by the addition of 0.1 μCi 3-hydroxy-3-methyl-[3-$^{14}$C]glutaryl coenzyme A (52 Ci/Mole) followed by incubating the complete reaction at 37° C. for 10 minutes. At the end of this period the reaction is stopped by adding 300 μl of a 10 mM mevalonolactone solution in 0.1 M hydrochloric acid and the mevalonic acid product allowed to lactonise for a further period of 30 minutes. The product is then isolated by chromatography using Bio-Rex 5 resin and the enzyme activity quantified by liquid scintillation spectrophotometry.

Appropriate controls are included in the assay and IC$_{50}$ values obtained by graphical means. The results are shown in Table 1 below.

EXAMPLE 22

Pharmacology

ASSAY FOR THE INHIBITION OF CHOLESTEROL BIOSYNTHESIS IN CULTURED CELLS

Human hepatoma (HEP G$_2$) or fibroblastic (HES-9) cells were grown in Dulbecco's modified Eagle's medium (DMEM) with 10% foetal calf serum, in 6 cm tissue culture dishes until approaching confluence (approximately 4 days). The medium was changed to DMEM with 1% foetal calf serum 24 hours prior to experimentation.

Test compounds that are salts were dissolved in aqueous, physiological buffer. Lactones and esters were dissolved in dimethylsulphoxide.

Test compound were added to the cell monolayers concurrently with 2-$^{14}$C-acetate (5 μCi/ml of incubation volume); control samples receiving vehicle together with radioisotope. The incubation was continued for 3 hours at 37° C.

Incorporation of $^{14}$C-acetate into non-saponifiable, digitonin-precipitable sterols in control samples continued in a linear manner beyond 3 hours.

The IC$_{50}$ for inhibition of sterol synthesis by test compounds was measured from plots of % inhibition (compared to controls) versus log concentration, using at least 5 concentrations of inhibitor.

This assay, therefore, measures the ability of test substances to inhibit intracellular synthesis of cholesterol.

Representative of the intrinsic HMG-CoA reductase inhibitory activities of the claimed compound are the IC$_{50}$s, tabulated below for a number of the compounds of the invention in both tests, expressed in nonomolar concentrations.

TABLE 1

| Example Number | Test A | Test B (HEP G$_2$) |
| --- | --- | --- |
| 3 (Compound G) (after hydrolysis) | 4 | 25 |
| 7 (Compound N) | 3 | 7 |

TABLE 1-continued

| Example Number | Test A | Test B (HEP G$_2$) |
| --- | --- | --- |
| 9 (Compound B) | 15 | 60 |
| Dihydromevinolin (prior art) | 30 | 40 |

Examples of unit dosage compositions are as follows:

EXAMPLE 23

Capsules

| | Ingredients | Per Capsule | Per 10,000 Capsules |
| --- | --- | --- | --- |
| 1. | Active ingredient (Cpd of Formula I) | 40.0 mg | 400 g |
| 2. | Lactose | 150.0 mg | 1500 g |
| 3. | Magnesium stearate | 4.0 mg | 40 g |
| | | 194.0 mg | 1940 g |

Procedure for capsules

Step 1. Blend ingredients No. 1 and No. 2 in a suitable blender.

Step 2. Pass blend from Step 1 through a No. 30 mesh (0.59 mm) screen.

Step 3. Place screened blend from Step 2 in a suitable blender with ingredient No. 3 and blend until the mixture is lubricated.

Step 4. Fill into No. 1 hard gelatin capsule shells on a capsule machine.

EXAMPLE 24

Tablets

| | Ingredients | Per Tablet | Per 10,000 Tablets |
| --- | --- | --- | --- |
| 1. | Active ingredient (Cpd of Form. I) | 40.0 mg | 400 g |
| 2. | Corn Starch | 20.0 mg | 200 g |
| 3. | Alginic acid | 20.0 mg | 200 g |
| 4. | Sodium alginate | 20.0 mg | 200 g |
| 5. | Magnesium stearate | 1.3 mg | 13 g |
| | | 101.3 mg | 1013 g |

Procedure for tablets

Step 1. Blend ingredients No. 1, No. 2, No. 3 and No. 4 in a suitable mixer/blender.

Step 2. Add sufficient water portionwise to the blend from Step 1 with careful mixing after each addition. Such additions of water and mixing until the mass is of a consistency to permit its conversion to wet granules.

Step 3. The wet wall is converted to granules by passing it through an oscillating granulator using a No. 8 mesh (2.38 mm) screen.

Step 4. The wet granules are then dried in an oven at 140° F. (60° C.) until dry.

Step 5. The dry granules are lubricated with ingredients No. 5.

Step 6. The lubricated granules are compressed on a suitable tablet press.

EXAMPLE 25

Intramuscular Injection

| | Ingredient | Per ml. | Per liter |
| --- | --- | --- | --- |
| 1. | Formula I compound Active ingredient | 10.0 mg | 10 g |
| 2. | Istonic buffer solution pH 4.0. | q.s. | q.s. |

Procedure

Step 1. Dissolve the active ingredient in the buffer solution.

Step 2. Aseptically filter the solution from Step 1.

Step 3. The sterile solution is now aseptically filled into sterile ampoules.

Step 4. The ampoules are sealed under aspetic conditions.

EXAMPLE 26

Suppositories

| | Ingredients | Per Supp. | Per 1,000 Supp |
| --- | --- | --- | --- |
| 1. | Formula I compound Active ingredient | 40.0 mg | 40 g |
| 2. | Polyethylene Glycol 1000 | 1350.0 mg | 1,350 g |
| 3. | Polyethylene Glycol 4000 | 450.0 mg | 450 g |
| | | 1840.0 mg | 1,840 g |

Procedure

Step 1. Melt ingredient No. 2 and No. 3 together and stir until uniform.

Step 2. Dissolve ingredient No. 1 in the molten mass from Step 1 and stir until uniform.

Step 3. Pour the molten mass from Step 2 into suppository moulds and chill.

Step 4. Remove the suppositories from moulds and wrap.

We claim:

1. A compound of either of general formulae I and II

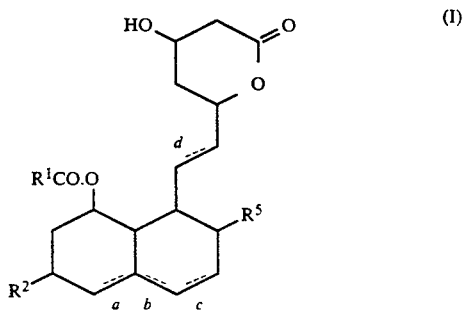

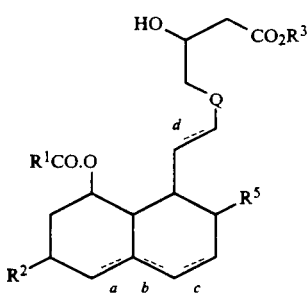

wherein:

- R¹ represents a C$_{1-8}$ alkyl, C$_{3-8}$ cycloalkyl, C$_{3-8}$ cycloalkyl (C$_{1-8}$) alkyl, C$_{2-8}$ alkenyl, or C$_{1-6}$ alkyl substituted phenyl group;
- R² represents a C$_{2-8}$ alkenyl, C$_{2-8}$ alkynyl, group or C$_{2-5}$ alkenyl, or C$_{2-5}$ alkynyl group substituted with a phenyl or substituted phenyl group;
- R³ represents a hydrogen atom or a substituent R⁴ or M;
- R⁴ represents a C$_{1-5}$ alkyl group, or a C$_{1-5}$ alkyl group substituted with a group chosen from substituted phenyl, dimethylamino and acetylamino; wherein substituted phenyl is phenyl substituted with C$_{1-6}$ alkyl, C$_{1-6}$ alkoxy, hydroxy, thiol amino, halo, trifluoromethyl or nitro;
- R⁵ represents a hydrogen atom or a methyl or ethyl group;
- M represents a cation capable of forming a pharmaceutically acceptable salt;
- Q represents C=O or CHOH; and each of a, b, c, and d is independently a single or double bond except that when a and c are double bonds then b is a single bond.

2. A compound as claimed in claim 1, which has one or more of the following substituents independently or in any combination:
- R¹ represents C$_{4-6}$ branched alkyl;
- R² represents C$_{2-5}$ alkenyl or C$_{2-5}$ alkenyl substituted with phenyl or substituted phenyl;
- R³ is R⁴;
- R⁴ represents C$_{1-5}$ alkyl;
- Q represents CHOH; and/or
- b and d are both single bonds, and one or both of a and c are double bonds.

3. A compound according to claim 1, wherein R¹ represents a C$_{4-6}$ branched alkyl group; R² represents a C$_{2-6}$ alkenyl group; each of a and c independently represents a single or double bond; and each of b and d represents a single bond.

4. A compound selected from the group consisting of:
(1S,2S,4aR,6S,8S,8aS,4'R,6'R,2"S)-6'-(2-(1,2,4a,5,6,7,8,8a-octahydro-2-methyl-8[(2"-methyl-1"-oxobutyl)oxy]-6-[(Z)-prop-1-enyl]-1-naphthalenyl)-ethyl}-tetrahydro-4'-hydroxy-2H-pyran-2'-one;

Sodium (1S,2S,4aR,6S,8S,8aS,3'R,5'r,2"S)-7'-(1,2,4a,5,6,7,8,8a-octahydro-2-methyl-8-[(2"-methyl-1"-oxobutyl)oxy]-6-[(Z)-prop-1-enyl]-1-naphthalenyl)-3',5'-dihydroxyheptanoate;

(1S,2S,4aR,6S,8S,8aS,4'R,6'R)-6'-{2-(1,2,4a,5,6,7,8,8a-octahydro-2-methyl-8-["2",2"-dimethyl-1"-oxobutyl)-oxy]-6[(Z)-prop-enyl]-1-naphthalenyl)ethyl}-tetra-hydro-4'-hydroxy-2H-pyran-2'-one;

(1S,2S,4aR,6S,8S,8aS,4'R,6'R)-6'-{2-(1,2,4a,5,6,7,8,8a-octahydro-2-methyl-8-[("2",2"-dimethyl-1"-oxobutyl)-oxy]-6-[(E)-but-1-enyl]-1-naphthalenyl)ethyl}-tetra-hydro-4'-hydroxy-2H-pyran-2'-one;

(1S,2S,4aR,6S,8S,8aS,4'R,6'R,2"S)-6'-{2-(1,2,4a,5,6,7,8,8a-octahydro-2-methyl-8-[(2"-methyl-1"-oxobutyl)-oxy]-6-[(E)-hex-1-enyl]-1-naphthalenyl)ethyl}-tetra-hydro-4'-hydroxy-2H-pyran-2'-one; or (1S,2S,4aR,6S,8S,8aS,4'R,6'R)-6'-{2-(1,2,4a,5,6,7,8a-octahydro-2-methyl-8-["2",2"-dimethyl-1"oxobutyl)-oxy]-6-[(E)]hex-1-enyl-1-naphthalenyl)ethyl)-tetra-hydro-4'-hydroxy-2H-pyran-2'-one.

5. A compound according to claim 3, wherein R¹ represents a C$_{4-5}$ branched alkyl group; R² represents (E)-prop-1-enyl; and R⁵ represents methyl.

6. A compound selected from the group consisting of:
(1S,2S,4aR,6S,8S,8aS,4'R,6'R,2"s)-6'-{2-(1,2,4a,5,6,7,8,8a-octahydro-2-methyl-8-[(2"-methyl-1"-oxobutyl)-oxy]-6[(E)-prop-1-enyl]-1-napthalenyl)ethyl}-tetrahydro-4'-hydroxy-2H-pyran-2'-one;

Methyl (1S,2S,4aR,6S,8S,8aS,3'R,2"S)-7'-(1,2,4a,5,6,7,8,8a-octahydro-2-methyl-8-[2"-methyl-1"-oxobutyl)oxy]-6-[(E)-prop-1-enyl]-1-naphthalenyl)-3',5'-dihydroxyheptanoate;

Methyl (1S,2S,4aR,6S,8S,8aS,3'R,2"S)-7'-(1,2,4a,5,6,7,8,8a-octahydro-2-methyl-8-[(2"-methyl-1"-oxobutyl)-oxy]-3[(E)-prop-1-enyl]-1-naphthalenyl)-3'-hydroxy-5'-oxoheptanoate;

(1S,2S,4aR,6S,8S,8aS,4'R,6'R)-6'-{2-(1,2,4a,5,6,7,8,-8a-octahydro-2-methyl-8-[("2",2"-dimethyl-1"-oxobutyl)-oxy]-6-[(E)-prop-1-enyl]-1-naphthalenyl)ethyl)-tetra-hydro-4'-hydroxy-2H-pyran-2'-one;

Methyl (1S,2S,4aR,6S,8S,8aS,3'R,5'R)-7'-(1,2,4a,5,6,7,8,8a-octahydro-2-methyl-8-["2",2"-dimethyl-1"-oxobutyl)oxy]-6-[(E)-prop-1-enyl]-1-naphthalenyl)-3',5'-dihydroxyheptanoate;

Methyl (1S,2S,4aR,6S,8S,8aS,3'R)-7'-(1,2,4a,5,6,7,8,8a-octahydro-2-methyl-8-["2",2"-diimethyl-1"-oxobutyl)oxy]-6-[(E)-prop-1-enyl]-1-naphthalenyl)-3'-hydroxy-5'-oxoheptanoate; or Sodium (1S,2S,4aR,6S,8S,8aS,3'R,5'R)-7'-(1,2,4a,5,6,7,8,8a-octahydro-2-methyl-8-[("2",2"-dimethyl-1"-oxobutyl)oxy]-6-[(E)-prop-1-enyl]-1-naphthalenyl)-3',5'-dihydroheptanoate.

7. A compound according to claim 1, wherein R¹ represents a C$_{4-6}$ branched alkyl group; R² represents a C$_{2-5}$ alkenyl substituted by a phenyl or substituted phenyl group; each of a and c independently represents a single or double bond; and each of b and d represents a single bond.

8. A compound according to claim 7, wherein R¹ represents a branched C$_4$ alkyl group; R² represents prop-1-enyl; R³ represents methyl or ethyl; R⁵ represents methyl; and Q represents the group CHOH.

9. A compound selected form the group consisting of:
1S,2S,4aR,6S,8S,8aS,4'R,6'R,2"S)-6'-(2-(1,2,4a,-5,6,7,8,8a-octahydro-2-methyl-8-[2"-methyl-1"-oxobutyl)oxy]-6-[3-phenyl-(E)-prop-1-enyl]-1-naphthalenyl)ethyl}-tetrahydro-4'-hydroxy-2H-pyran-2'-one; or (1S,2S,4aR,6S,8S,8aS,4'R,6'R)-6'-(2-(1,2,4a,5,6,7,-8,8a-octahydro-2-methyl-8-("2",2"-dimethyl-1"-oxobutyl)-oxy]-6-[3-phenyl-(E)-prop-1-enyl]-1-naphthalenyl)-ethyl}-tetrahydro-4'-hydroxy-2H-pyran-2'-one.

10. A pharmaceutical composition comprising a compound as defined in any one of claims 1 to 9, or a mixture of such compounds, and a pharmaceutically acceptable carrier therefor.

11. A composition as claimed in claim 10 comprising a pharmaceutically acceptable non-toxic cation polymer capable of binding bile acids in a non-reabsorbable form in the gastrointestinal tract.

12. A compound of the formula

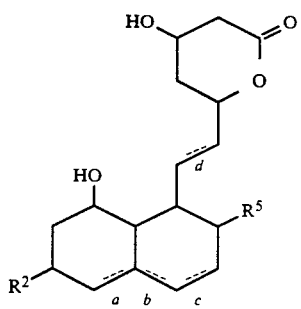

wherein $R_2$ and $R_5$ and a, b, c and d are as defined in claim 1.

13. A compound of the formula:

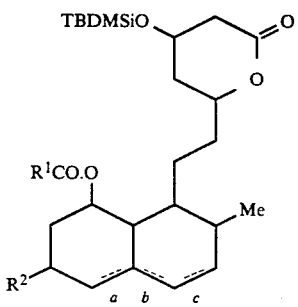

wherein $R^1$, $R^2$, $R^4$ and $R^5$, and a, b and c are as defined in claim 1 and $P^2$ is t-butyldimethylsilyl protecting group.

14. A compound of the formula wherein $R^1$ and $R^2$, a, b and c are as defined in claim 1.

* * * * *